(12) United States Patent
Das et al.

(10) Patent No.: US 6,962,915 B2
(45) Date of Patent: Nov. 8, 2005

(54) PYRAZOLO-PYRIMIDINE ANILINE COMPOUNDS USEFUL AS KINASE INHIBITORS

(75) Inventors: Jagabandhu Das, Mercerville, NJ (US); Chunjian Liu, Pennington, NJ (US); Robert V. Moquin, East Brunswick, NJ (US); Katerina Leftheris, Skillman, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/440,864

(22) Filed: May 19, 2003

(65) Prior Publication Data

US 2004/0023992 A1 Feb. 5, 2004

Related U.S. Application Data

(60) Provisional application No. 60/382,014, filed on May 20, 2002.

(51) Int. Cl.[7] .................. C07D 487/04; A61K 31/519; A61P 19/02
(52) U.S. Cl. .................. 514/234.2; 544/118; 544/262; 540/575; 514/211.08; 514/262.1; 548/371.7
(58) Field of Search .................. 514/234.2, 211.08, 514/262.1; 544/118, 262; 540/575

(56) References Cited

U.S. PATENT DOCUMENTS

| 5,593,997 | A | | 1/1997 | Dow et al. | |
|---|---|---|---|---|---|
| 5,723,608 | A | * | 3/1998 | Yuan | 544/262 |
| 6,147,080 | A | | 11/2000 | Bemis et al. | |
| 6,277,989 | B1 | | 8/2001 | Chakravarty et al. | |
| 6,548,509 | B2 | * | 4/2003 | Yuan | 514/262.1 |
| 6,670,357 | B2 | | 12/2003 | Leftheris et al. | |
| 2003/0232831 | A1 | | 12/2003 | Dyckman et al. | |
| 2004/0082582 | A1 | | 4/2004 | Dyckman et al. | |

FOREIGN PATENT DOCUMENTS

| WO | WO94/13677 | 6/1994 |
|---|---|---|
| WO | WO99/15164 | 4/1999 |
| WO | WO 00/56738 | 9/2000 |
| WO | WO 00/71129 | 11/2000 |
| WO | WO 01/14378 | 3/2001 |
| WO | WO 01/27089 | 4/2001 |
| WO | WO 01/34605 | 5/2001 |
| WO | WO02/12226 | 2/2002 |
| WO | WO02/12227 | 2/2002 |
| WO | WO02/12228 | 2/2002 |
| WO | WO02/16348 | 2/2002 |

OTHER PUBLICATIONS

Figure 13–4: Cytokines http://www.whfreeman.com/immunology/CH13/cytokines.htm Downloaded from the Internet Jul. 15, 2003.*
Boehm, Expert Opinion Therapeutic Patents (2000) 10(1) 25.*
Henry et al., Drug. Fut., vol. 24, pp. 1345–1354 (1999).
Rankin et al., Br. J. Rheumatol., vol. 34, pp. 334–342 (1995).
Moreland et al., Ann. Intern. Med., vol. 130, pp. 478–486 (1999).

* cited by examiner

*Primary Examiner*—Mark L. Berch
(74) *Attorney, Agent, or Firm*—Joseph C. Wang; Elliott Korsen; Anastasia P. Winslow

(57) ABSTRACT

Compounds having the formula (I),

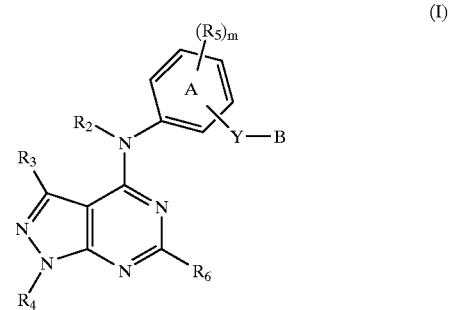

and pharmaceutically acceptable salts or prodrugs thereof, are useful as kinase inhibitors, wherein Y is —C(=O)NR$_1$—, —NR$_1$C(=O)—, —NR$_1$C(=O)NR$_1$—, —NR$_1$SO$_2$—, —SO$_2$NR$_1$—, —C(=O)—, —OC(=O)—, or —CO$_2$—; B is alkyl, substituted alkyl, alkenyl, substituted alkenyl, hydroxy, alkoxy, aryl, cycloalkyl, heteroaryl, and heterocyclo; or when Y is —C(=O)NR$_1$—, B also may be selected from —C(=O)R$_8$, —C(=O)NR$_8$R$_9$, and —CO$_2$R$_8$; R$_1$ is hydrogen, C$_{1-4}$alkyl, or substituted C$_{1-4}$alkyl; R$_2$ is hydrogen or C$_{1-4}$alkyl; R$_3$ is hydrogen, methyl, perfluoromethyl, hydroxy, methoxy, halogen, cyano, NH$_2$, or NH(CH$_3$); and R$_4$, R$_5$, R$_6$, R$_7$, R$_8$, and R$_9$ are as defined in the specification.

17 Claims, No Drawings

PYRAZOLO-PYRIMIDINE ANILINE COMPOUNDS USEFUL AS KINASE INHIBITORS

This application claims priority to U.S. Provisional Application Ser. No. 60/382,014 filed May 20, 2002, the entirety of which is incorporated herein by reference.

FIELD OF THE INVENTION

This invention relates to pyrazolo-pyrimidine compounds, more particularly, to aniline-substituted pyrazolo-pyrimidine compounds useful for treating p38 kinase-associated conditions. The invention further pertains to pharmaceutical compositions containing at least one compound according to the invention useful for treating p38 kinase-associated conditions and methods of inhibiting the activity of p38 kinase in a mammal.

BACKGROUND OF THE INVENTION

A large number of cytokines participate in the inflammatory response, including IL-1, IL-6, IL-8 and TNF-α. Overproduction of cytokines such as IL-1 and TNF-α are implicated in a wide variety of diseases, including inflammatory bowel disease, rheumatoid arthritis, psoriasis, multiple sclerosis, endotoxin shock, osteoporosis, Alzheimer's disease, and congestive heart failure, among others [Henry et al., *Drugs Fut.*, 24:1345–1354 (1999); Salituro et al., *Curr. Med. Chem.*, 6:807–823 (1999)]. Evidence in human patients indicates that protein antagonists of cytokines are effective in treating chronic inflammatory diseases, such as, for example, monoclonal antibody to TNF-α (Enbrel) [Rankin et al., *Br. J. Rheumatol.*, 34:334–342 (1995)], and soluble TNF-α receptor-Fc fusion protein (Etanercept) [Moreland et al., *Ann. Intern. Med.*, 130:478–486 (1999)].

The biosynthesis of TNF-α occurs in many cell types in response to an external stimulus, such as, for example, a mitogen, an infectious organism, or trauma.

Important mediators of TNF-α production are the mitogen-activated protein (MAP) kinases, and in particular, p38 kinase. These kinases are activated in response to various stress stimuli, including but not limited to proinflammatory cytokines, endotoxin, ultraviolet light, and osmotic shock. Activation of p38 requires dual phosphorylation by upstream MAP kinase kinases (MKK3 and MKK6) on threonine and tyrosine within a Thr-Gly-Tyr motif characteristic of p38 isozymes.

There are four known isoforms of p38, i.e., p38-α, p38β, p38γ, and p38δ. The α and β isoforms are expressed in inflammatory cells and are key mediators of TNF-α production. Inhibiting the p38α and β enzymes in cells results in reduced levels of TNF-α expression. Also, administering p38α and β inhibitors in animal models of inflammatory disease has proven that such inhibitors are effective in treating those diseases. Accordingly, the p38 enzymes serve an important role in inflammatory processes mediated by IL-1 and TNF-α. Compounds that reportedly inhibit p38 kinase and cytokines such as IL-1 and TNF-α for use in treating inflammatory diseases are disclosed in U.S. Pat. Nos. 6,277,989 and 6,130,235 to Scios, Inc; U.S. Pat. Nos. 6,147,080 and 5,945,418 to Vertex Pharmaceuticals Inc; U.S. Pat Nos. 6,251,914, 5,977,103 and 5,658,903 to SmithKline Beecham Corp.; U.S. Pat. Nos. 5,932,576 and 6,087,496 to G. D. Searle & Co.; WO 00/56738 and WO 01/27089 to Astra Zeneca; WO 01/34605 to Johnson & Johnson; WO 00/12497 (quinazoline derivatives as p38 kinase inhibitors); WO 00/56738 (pyridine and pyrimidine derivatives for the same purpose); WO 00/12497 (discusses the relationship between p38 kinase inhibitors); and WO 00/12074 (piperazine and piperidine compounds useful as p38 inhibitors).

The present invention provides pyrazolo-pyrimidine compounds, particularly, pyrazolo-pyrimidine aniline compounds useful as kinase inhibitors, particularly kinases p38α and β. Methods of treating p38 kinase-associated conditions as well as pyrrolotriazine compounds useful for that purpose are described in U.S. patent application Ser. No. 10/036,293, assigned to the present assignee and having common inventors herewith, which claims the benefit of U.S. Provisional Application No. 60/249,877, filed Nov. 17, 2000, and U.S. Provisional Application No. 60/310,561, filed Aug. 7, 2001; and U.S. Patent Application Ser. Nos. 60/374,907 and 60/374,938, both filed Apr. 23, 2002, also assigned to the present assignee and having common inventors herewith. Each of the patent applications, patents, and publications referred to herein is incorporated by reference.

SUMMARY OF THE INVENTION

The instant invention pertains to compounds of formula (I), useful as inhibitors of p38 kinase,

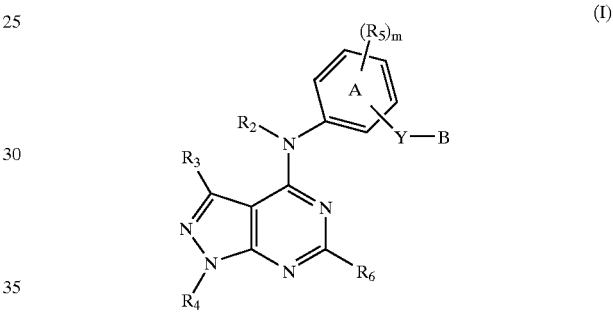

(I)

and pharmaceutically-acceptable salts, prodrugs, or solvates thereof, wherein:

Y is —C(=O)NR$_1$—, —NR$_1$C(=O)—, —NR$_1$C(=O)NR$_1$—, —NR$_1$SO$_2$—, —SO$_2$NR$_1$—, —C(=O)—, —OC(=O)—, or —CO$_2$—;

B is selected from alkyl, substituted alkyl, alkenyl, substituted alkenyl, hydroxy, alkoxy, aryl, cycloalkyl, heteroaryl, and heterocyclo; or when Y is —C(=O)NR$_1$—, B also may be selected from —C(=O)R$_8$, —C(=O)NR$_8$R$_9$, and —CO$_2$R$_8$, R$_1$ is hydrogen, C$_{1-4}$alkyl, or substituted C$_{1-4}$alkyl;

R$_2$ is hydrogen or C$_{1-4}$alkyl;

R$_3$ is hydrogen, methyl, perfluoromethyl, hydroxy, methoxy, halogen, cyano, NH$_2$, or NH(CH$_3$);

R$_4$ is hydrogen, alkyl, substituted alkyl, alkenyl, substituted alkenyl, aryl, cycloalkyl, heteroaryl, or heterocyclo;

R$_5$ is selected from hydrogen, halogen, cyano, alkyl, substituted alkyl, —C(=O)R$_{11}$, —CO$_2$R$_{11}$, —S(=O)R$_{12}$, —SO$_2$R$_{12}$, —SO$_3$R$_{12}$, —OR$_{11}$, —SR$_{11}$, —NR$_{11}$R$_{12}$, —C(=O)NR$_{11}$R$_{12}$, —NR$_{11}$C(=O)R$_{12}$, NR$_{11}$CO$_2$R$_{12}$, —NR$_{11}$SO$_2$R$_{12}$, —SO$_2$NR$_{11}$R$_{12}$, cycloalkyl, aryl, heterocyclo and heteroaryl;

R$_6$ is selected from halogen, cyano, nitro, A$_1$-R$_{13}$, -A$_1$-O-A$_2$-R$_{13}$, -A$_1$-S-A$_2$-R$_{13}$, -A$_1$-C(=O)-A$_2$-R$_{13}$, -A$_1$-OC(=O)-A$_2$-R$_{13}$, -A$_1$-S(=O)-A$_2$-R$_{13}$, -A$_1$-SO$_2$-A$_2$-R$_{13}$, -A$_1$-CO$_2$-A$_2$-R$_{13}$, -A$_1$-NR$_{13}$-A$_2$-R$_{14}$, -A$_1$-NR$_{15}$C(=O)-A$_2$-R$_{13}$, -A$_1$-NR$_{15}$C(=O)NR$_{16}$-A$_2$-R$_{13}$, -A$_1$-NR$_{15}$CO$_2$-A$_2$-R$_{13}$, -A$_1$-NR$_{15}$SO$_2$-A$_2$-R$_{13}$, -A$_1$-NR$_{15}$SO$_2$NR$_{16}$-A$_2$-R$_{13}$, -A$_1$-SO$_2$NR$_{15}$-A$_2$-R$_{13}$, and -A$_1$-C(=O)NR$_{15}$-A$_2$-R$_{13}$;

$A_1$ is —$(CR_{17}R_{18})_r$—;

$A_2$ is —$(CR_{19}R_{20})_s$—;

$R_8$ and $R_9$ are selected from hydrogen, alkyl, substituted alkyl, aryl, cycloalkyl, heteroaryl, and heterocyclo, or when attached to the same nitrogen atom may together form a heteroaryl or heterocyclo ring;

$R_{11}$, $R_{12}$, $R_{13}$, and $R_{14}$ are selected from hydrogen, alkyl, substituted alkyl, alkenyl, substituted alkenyl, aryl, cycloalkyl, heteroaryl, and heterocyclo, or when attached to the same nitrogen atom may form a heteroaryl or heterocyclo ring, provided that when $R_{12}$ or $R_{13}$ is attached to a sulfonyl group (as in —S(=O)$R_{12}$, —SO$_2R_{12}$, —SO$_3R_{12}$, -$A_1$-S(=O)$R_{13}$, -$A_1$-SO$_2R_{13}$, and -$A_1$-SO$_3R_{13}$), $R_{12}$ and $R_{13}$ are not hydrogen;

$R_{15}$ and $R_{16}$ are selected from hydrogen, $C_{1-4}$alkyl, hydroxy, hydroxy$C_{1-4}$alkyl, and amino$C_{1-4}$alkyl;

$R_{17}$, $R_{18}$, $R_{19}$, and $R_{20}$ are selected from hydrogen, $C_{1-4}$alkyl, halogen, cyano, hydroxy, hydroxy$C_{1-4}$alkyl, halo$C_{1-4}$alkyl, $C_{1-4}$haloalkoxy, amino, $C_{1-4}$alkylamino, and amino$C_{1-4}$alkyl;

m is 0, 1 or 2; and r and s are selected from 0, 1, 2, 3, and 4.

The invention further pertains to pharmaceutical compositions containing compounds of formula (I), and to methods of treating conditions associated with the activity of p38 kinase ($\alpha$ and $\beta$), comprising administering to a mammal a pharmaceutically-acceptable amount of a compound of formula (I).

DESCRIPTION OF THE INVENTION

Listed below are definitions of various terms used to describe this invention. These definitions apply to the terms as they are used throughout this specification, unless otherwise limited in specific instances, either individually or as part of a larger group.

The term "alkyl" refers to straight or branched chain hydrocarbon groups having 1 to 12 carbon atoms, preferably 1 to 8 carbon atoms, such as methyl, ethyl, n-propyl, i-propyl, n-butyl, i-butyl, t-butyl, pentyl, hexyl, heptyl, octyl, etc. Lower alkyl groups, that is, alkyl groups of 1 to 4 carbon atoms, are most preferred.

The term "substituted alkyl" refers to alkyl groups substituted with one, two or three groups selected from halogen, cyano, keto (=O), —OR$_a$, —SR$_a$, —NR$_a$R$_b$, —(C=O)R$_a$, —CO$_2$R$_a$, —C(=O)NR$_a$R$_b$, —NR$_a$C(=O)R$_b$, —NR$_a$CO$_2$R$_b$, —OC(=O)R$_a$, —OC(=O)NR$_a$R$_b$, —NR$_a$C(=O)NR$_a$R$_b$, —SO$_2$NR$_a$R$_b$, —NR$_a$SO$_2$R$_d$, —SO$_2$R$_d$, —SO$_3$R$_d$, cycloalkyl, aryl, heteroaryl, and heterocyclo, wherein the groups R$_a$, R$_b$, and R$_c$ are selected from hydrogen, $C_{1-6}$alkyl, cycloalkyl, aryl, heteroaryl, heterocycle, or $C_{1-6}$alkyl or $C_{2-6}$alkenyl substituted with one, two or three of halogen, hydroxy, O(alkyl), haloalkoxy, O(phenyl), O(benzyl), nitro, cyano, —(C=O)H, —CO$_2$H, —(C=O)alkyl, —CO$_2$alkyl, —(C=O)cycloalkyl, —CO$_2$cycloalkyl, —C(=O)phenyl, —CO$_2$phenyl, —NH$_2$, —NH(alkyl), —N(alkyl)$_2$, —NH(cycloalkyl), —NH(aryl), —NH(heterocyclo), —SH, —S(alkyl), —(C=O)NH$_2$, —(C=O)NH(alkyl), —(C=O)NH(cycloalkyl), —(C=O)N(alkyl)$_2$, SO$_2$(alkyl), phenyl, benzyl, $C_{3-7}$cycloalkyl, four to seven membered heterocyclo, and/or five or six membered heteroaryl. The group R$_d$ may be selected from the same groups as R$_a$, R$_b$ and R$_c$, but is not hydrogen. Alternatively, the groups R$_a$ and R$_b$ may together form a heterocyclo or heteroaryl ring. It should be understood that when a substituted alkyl group is substituted with an aryl, cycloalkyl, heteroaryl, or heterocyclo, such rings are as defined below and thus may have one to three substituents as set forth below in the definitions for these terms.

When the term "alkyl" is used as a suffix following another specifically-named group, e.g., arylalkyl, heteroarylalkyl, hydroxyalkyl, the term defines with more specificity at least one of the substituents that the substituted alkyl will contain. For example, arylalkyl refers to an aryl bonded through an alkyl, or in other words, a substituted alkyl group having from 1 to 12 carbon atoms and at least one substituent that is aryl (e.g., benzyl or biphenyl). "Lower arylalkyl" refers to substituted alkyl groups having 1 to 4 carbon atoms and at least one aryl substituent. It should be understood that when reference is made to an arylalkyl, heteroarylalkyl, cycloalkylalkyl, or heterocycloalkyl, the ringed groups are as defined below and thus may optionally be substituted, as defined below, and the alkyl groups optionally may have one or two other substituents selected from those recited above for substituted alkyl groups.

When a subscript is used in conjunction with a group such as $C_{1-4}$alkyl, the subscript refers to the number of carbon atoms that the group will contain, in addition to heteroatoms. Thus, the term hydroxy$C_{1-4}$alkyl or $C_{1-4}$hydroxyalkyl refers to an alkyl group of one to four carbon atoms having an OH substituent on one of the carbon atoms. As another example, the term $C_{1-2}$alkylamino refers to an alkylamino group having one or two carbon atoms, i.e., —NHCH$_3$, —N(CH$_3$)$_2$, or —NHCH$_2$CH$_3$.

The term "alkenyl" refers to straight or branched chain hydrocarbon groups having 2 to 12 carbon atoms and at least one double bond. Alkenyl groups of 2 to 6 carbon atoms and having one double bond are most preferred.

The term "alkynyl" refers to straight or branched chain hydrocarbon groups having 2 to 12 carbon atoms and at least one triple bond. Alkynyl groups of 2 to 6 carbon atoms and having one triple bond are most preferred. A "substituted alkenyl" or "substituted alkynyl" will contain one, two, or three substituents as defined above for alkyl groups.

The term "alkylene" refers to bivalent straight or branched chain hydrocarbon groups having 1 to 12 carbon atoms, preferably 1 to 8 carbon atoms, e.g., {—CH$_2$—}$_n$, wherein n is 1 to 12, preferably 1–8. Lower alkylene groups, that is, alkylene groups of 1 to 4 carbon atoms, are most preferred. The terms "alkenylene" and "alkynylene" refer to bivalent radicals of alkenyl and alknyl groups, respectively, as defined above. Substituted alkylene, alkenylene, and alkynylene groups may have substituents as defined above for the monovalent groups.

The term "alkoxy" refers to the group ORe wherein Re is alkyl. The term "aryloxy" refers to the groups O(aryl) and O(heteroaryl), wherein aryl and heteroaryl are as defined below.

The term "alkylthio" refers to an alkyl or substituted alkyl group as defined above bonded through one or more sulfur (—S—) atoms, e.g., —S(alkyl) or —S(substituted alkyl).

The term "alkylamino" refers to the groups —NHR$_f$ and NR$_f$R$_g$, wherein R$_f$ and R$_g$ are alkyl or substituted alkyl as defined above. "Aminoalkyl" refers to an amino group bonded through an alkyl, e.g., —(CH$_2$)$_x$—NH$_2$. "Alkylaminoalkyl" refers to an alkylamino group (i.e., —NHR$_f$ or NR$_f$R$_g$) bonded through an alkyl group (e.g., —(CH$_2$)$_x$—NHR$_f$ or —(CH$_2$)$_x$—NR$_f$R$_g$).

The term "acyl" refers to an alkyl or substituted alkyl group as defined above bonded through one or more carbonyl {—C(=O)—} groups. When the term acyl is used in conjunction with another group, as in acylamino, this refers to the carbonyl group {—C(=O)} linked to the second named group. Thus, for example, acylamino refers to —C(=O)NH$_2$ and acylaryl refers to —C(=O)(aryl).

The term "halo" or "halogen" refers to chloro, bromo, fluoro and iodo.

The term carbamyl refers to the group $C(=O)NR_hR_i$ wherein $R_h$ and $R_i$ may be selected from hydrogen, alkyl, and substituted alkyl.

The term "carboxy" when used alone refers the group $CO_2H$. "Carboxyalkyl" refers to the group $CO_2R_f$, wherein $R_f$ is alkyl or substituted alkyl, as defined above.

The term "sulfonamide" or "sulfonamidyl" refers to the group $—S(O)_2NR_hR_i$, wherein $R_h$ and $R_i$ are as defined above for carbamyl.

The term "sulphonyl" or "sulfonyl" refers to the group $—S(O)_{1-2}R_f$, wherein $R_f$ is alkyl or substituted alkyl, as defined above.

The term "cycloalkyl" refers to monocyclic or bicyclic hydrocarbon groups of 3 to 9 carbon atoms which are fully saturated. The term "cycloalkyl" includes such saturated carbocyclic rings having a carbon-carbon bridge of three to four carbon atoms or having 1 or 2 aromatic or heterocyclo rings fused thereto. Thus, the term "cycloalkyl" includes, for example, cyclopropyl, cyclobutyl, cyclopentyl, cyclohexyl, cycloheptyl, cyclooctyl, etc., as well as

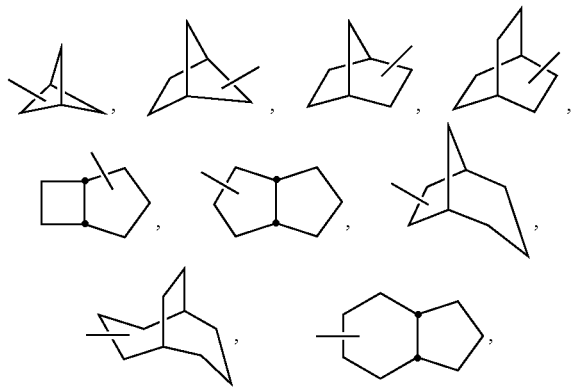

and the like.

Additionally, the term "substituted cycloalkyl" unless otherwise indicated includes cycloalkyl groups as defined above substituted with one, two or three groups selected from (i) $R_j$, (ii) keto (=O), and (iii) $C_{1-6}$alkyl or $C_{2-6}$alkenyl optionally substituted with one to three of $R_j$, wherein $R_j$ is halogen, nitro, cyano, haloalkyl, haloalkoxy, $—O-A-R_k$, $—S-A-R_k$, $—C(=O)-A-R_j$, $—OC(=O)-A-R_k$, $—S(=O)-A-R_k$, $—SO_2-A-R_k$, $—CO_2-A-R_k$, $—NR_j-A-R_k$, $—NR_nC(=O)-A-R_k$, $—NR_mC(=O)NR_n-A-R_k$, $—NR_mCO_2-A-R_k$, $—NR_mSO_2-A-R_k$, $—NR_nSO_2NR_n-A-R_k$, $—SO_2NR_m-A-R_k$, or $—C(=O)NR_mA-R_k$, phenyl or benzyl substituted with one to two $R_p$, $C_{3-7}$ cycloalkyl substituted with keto(=O) and/or one to two $R_p$, four to seven membered monocyclic or seven to eleven membered bicyclic heterocyclo substituted with keto(=O) and/or one to two $R_p$, and five to six membered monocyclic or nine or ten membered bicyclic heteroaryl substituted with one to two $R_p$, wherein A is $—(CR_mR_n)_w—$; w is 0 to 4; $R_m$ and $R_n$ are selected from hydrogen, alkyl, hydroxyalkyl, haloalkyl, amino, and aminoalkyl; $R_k$ is selected from hydrogen, alkyl, amino, alkylamino, phenyl, $C_{3-7}$ cycloalkyl, four to seven membered monocyclic or seven to eleven membered bicyclic heterocyclo, and five to six membered monocyclic or nine or ten membered bicyclic heteroaryl; wherein each $R_k$ in turn is optionally substituted with one to two $R_p$, and $R_p$ is at each occurrence independently selected from $C_{1-4}$alkyl, $C_{2-4}$alkenyl, $—O(C_{1-4}$alkyl), halogen, cyano, nitro, $—C_{1-4}$haloalkyl, $—O(C_{1-4}$haloalkyl), $—SH$, $—S(C_{1-4}$alkyl), $—SO_2(C_{1-4}$alkyl), $—CO_2H$, $—CO_2(C_{1-4}$alkyl), $—C(=O)H$, $—C(=O)(C_{1-4}$alkyl), $—NH_2$, $—NH(C_{1-6}$alkyl), $—N(C_{1-6}$alkyl)$_2$, phenyloxy, benzyloxy, and/or lower alkyl substituted with one to two hydroxy, halogen, cyano, $—O(C_{1-4}$alkyl), $—O(C_{2-4}$alkenyl), amino, $C_{1-4}$alkylamino, nitro, trifluoromethyl, trifluoromethoxy, $—S(C_{1-4}$alkyl), $—SO_2C_{1-4}$alkyl, $—CO_2H$, $—CO_2(C_{1-4}$alkyl), $—C(=O)H$, and/or $—C(=O)(C_{1-4}$alkyl).

The term "aryl" refers to phenyl, 1-naphthyl and 2-naphthyl, with phenyl being preferred, as well as such rings having fused thereto a cycloalkyl, cycloalkenyl, heterocyclo, or heteroaryl ring. Examples of aryl groups include, without limitation:

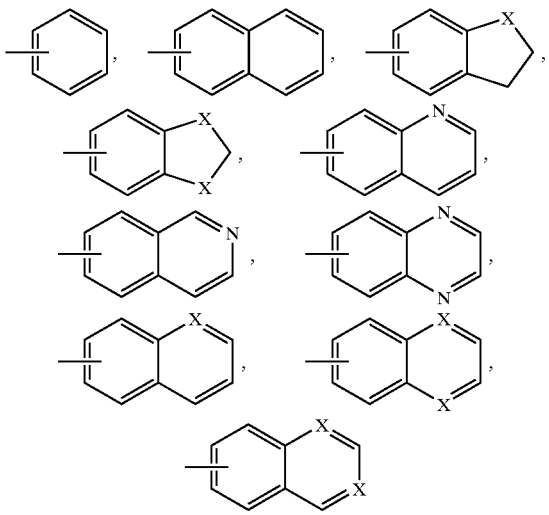

wherein X at each occurrence is selected from oxygen, nitrogen, and sulfur; and other like ring systems.

Additionally, the term "aryl" includes such rings having one, two or three substituents selected from (i) $R_j$, and (ii) $C_{1-6}$alkyl or $C_{2-6}$alkenyl optionally substituted with one to two of $R_j$ and/or keto (=O), wherein $R_j$ is as defined above for cycloalkyl and has the various optional substituents as defined above for cycloalkyl. When reference is made generally to a particular aryl, such as phenyl, it should be understood that unless otherwise indicated, such group may likewise have one, two or three substituents as defined for aryl.

The term "carbocyclo" or "carbocyclic" refers to a cyclic group in which all ring atoms are carbon, including substituted or unsubstituted cycloalkyl and aryl groups, as defined herein.

The term "heterocyclo" or "heterocycle" refers to non-aromatic 3 to 7 membered monocyclic groups, 7 to 11 membered bicyclic groups, and 10 to 15 membered tricyclic groups which have at least one heteroatom (O, S or N) in at least one of the rings. Each ring of the heterocyclo group containing a heteroatom can contain one or two oxygen or sulfur atoms and/or from one to four nitrogen atoms provided that the total number of heteroatoms in each ring is four or less, and further provided that the ring contains at least one carbon atom. Advantageously, adjacent heteroatoms will not be simultaneously selected from N and O. The rings completing the bicyclic and tricyclic groups may contain only carbon atoms and may be saturated, partially saturated, or unsaturated, and they may be either fused, bridged, and/or joined through one or more spiro unions.

The nitrogen and sulfur atoms may optionally be oxidized and the nitrogen atoms may optionally be quaternized. The heterocyclo group may be attached at any available nitrogen or carbon atom. Exemplary heterocyclo groups include, without limitation:

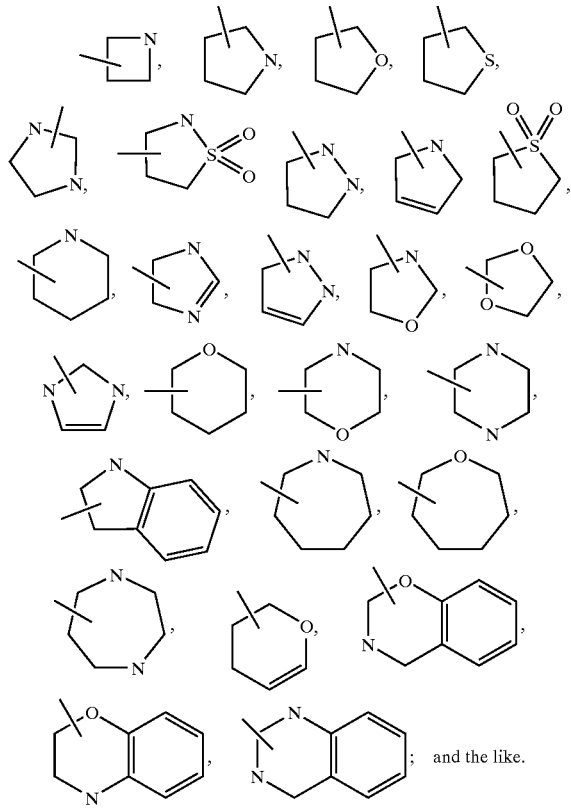

; and the like.

The term "heterocyclo" includes heterocyclo rings as defined containing one, two or three substituents at any available carbon or nitrogen atom selected from $R_j$, keto (=O), and $C_{1-6}$alkyl or $C_{2-6}$alkenyl optionally substituted with one to two of $R_j$ and/or keto (=O), wherein $R_j$ is as defined above for cycloalkyl and has the various optional substituents as defined above for cycloalkyl.

The term "heteroaryl" refers to aromatic 5 or 6 membered monocyclic groups, 9 or 10 membered bicyclic groups, and 11 to 14 membered tricyclic groups which have at least one heteroatom (O, S or N) in at least one of the rings. Each ring of the heteroaryl group containing a heteroatom can contain one or two oxygen or sulfur atoms and/or from one to four nitrogen atoms, provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. Examples of heteroaryl rings include, without limitation:

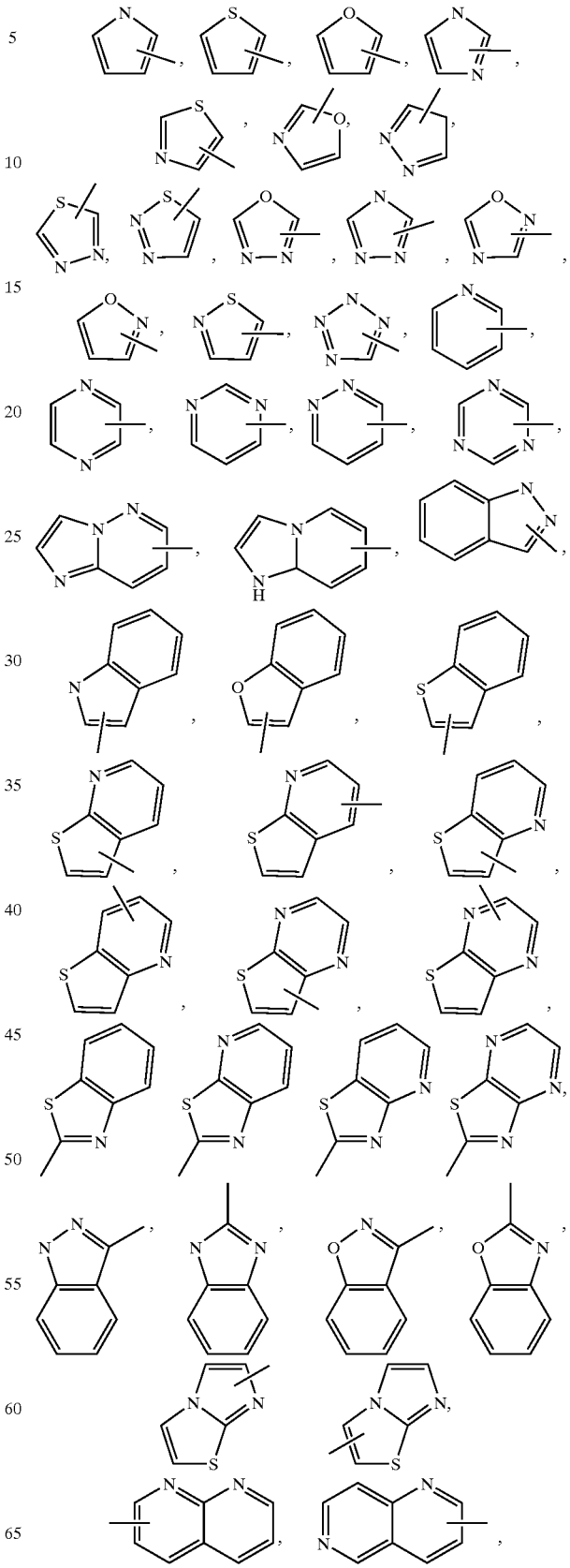

-continued

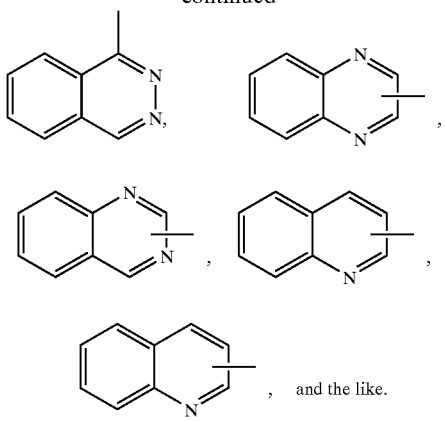
, and the like.

The term "heteroaryl" further includes such rings as defined above containing one, two or three substituents at any available carbon or nitrogen atom selected from (i) $R_j$, and (ii) $C_{1-6}$alkyl or $C_{2-6}$alkenyl optionally substituted with one to two of $R_j$ and/or keto (=O), wherein $R_j$ is as defined above for cycloalkyl and has the various optional substituents as defined above for cycloalkyl. When reference is made generally to a particular heteroaryl, such as thienyl or benzothienyl, it should be understood that unless otherwise indicated, such group may likewise have one, two or three substituents as defined for heteroaryl.

The term "heteroatoms" shall include oxygen, sulfur and nitrogen.

The term "haloalkyl" means an alkyl having one or more halo substituents. Thus, it includes, for example, trifluoromethyl. The term "perfluoromethyl" means a methyl group having two or three fluoro substituents.

The term "haloalkoxy" means an alkoxy group having one or more halo substituents. For example, "haloalkoxy" includes —OCF$_3$.

When the term "unsaturated" is used herein to refer to a ring or group, the ring or group may be fully unsaturated or partially unsaturated.

Throughout the specification, groups and substituents thereof may be chosen by one skilled in the field to provide stable moieties and compounds.

The compounds of Formula (I) may form salts which are also within the scope of this invention. Pharmaceutically acceptable (i.e. non-toxic, physiologically acceptable) salts are preferred, although other salts are also useful, e.g., in isolating or purifying the compounds of this invention.

The compounds of Formula (I) may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts can be formed as known to those skilled in the art.

The compounds for Formula (I) may form salts with a variety of organic and inorganic acids. Such salts include those formed with hydrogen chloride, hydrogen bromide, methanesulfonic acid, sulfuric acid, acetic acid, trifluoroacetic acid, oxalic acid, maleic acid, benzenesulfonic acid, toluenesulfonic acid and various others (e.g., nitrates, phosphates, borates, tartrates, citrates, succinates, benzoates, ascorbates, salicylates and the like). Such salts can be formed as known to those skilled in the art. Salt forms of the compounds may be advantageous for improving the compound dissolution rate and oral bioavailability.

In addition, zwitterions ("inner salts") may be formed.

All stereoisomers of the compounds of the instant invention are contemplated, either in admixture or in pure or substantially pure form. The definition of compounds according to the invention embraces all the possible stereoisomers and their mixtures. It embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

Compounds of the Formula (I) may also have prodrug forms. Any compound that will be converted in vivo to provide the bioactive agent (i.e., the compound for formula I) is a prodrug within the scope and spirit of the invention.

Various forms of prodrugs are well known in the art. For examples of such prodrug derivatives, see:

a) *Design of Prodrugs*, edited by H. Bundgaard, (Elsevier, 1985) and *Methods in Enzymology*, Vol.42, p. 309–396, edited by K. Widder, et al. (Acamedic Press, 1985);

b) *A Textbook of Drug Design and Development*, edited by Krosgaard-Larsen and H. Bundgaard, Chapter 5, "Design and Application of Prodrugs," by H. Bundgaard, p. 113–191 (1991); and c) H. Bundgaard, *Advanced Drug Delivery Reviews*, 8, 1–38 (1992), each of which is incorporated herein by reference.

It should further be understood that solvates (e.g., hydrates) of the compounds of Formula (I) are also with the scope of the present invention. Methods of solvation are generally known in the art.

Preferred Compounds

Preferred compounds are those having formula (Ia),

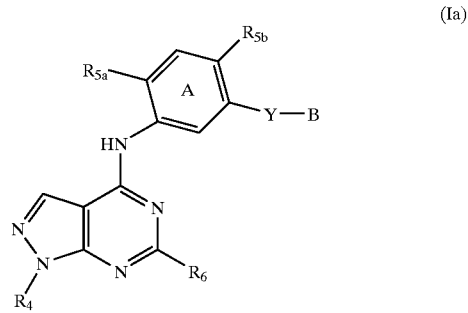

(Ia)

in which

Y is —C(=O)NH—, —C(=O)NH—, —NHC(=O)NH—, —NHSO$_2$—, or —SO$_2$NH—;

B is hydroxy, alkoxy, or an optionally-substituted aryl, cycloalkyl, heteroaryl, heterocyclo, arylalkyl, cycloalkylalkyl, heteroarylalkyl, or heterocycloalkyl;

R$_4$ is alkyl, substituted alkyl, or optionally-substituted aryl or heteroaryl;

R$_{5a}$ and R$_{5b}$ are independently selected from hydrogen, C$_{1-4}$alkyl, halogen, trifluoromethoxy, trifluoromethyl, hydroxy, C$_{1-4}$alkoxy, cyano, NH$_2$, NH(C$_{1-4}$alkyl), and N(C$_{1-4}$alkyl)$_2$;

R$_6$ is selected from hydrogen, alkyl, substituted alkyl, halogen, cyano, -A$_1$-O-A$_2$-R$_{13}$, -A$_1$-NR$_{13}$R$_{14}$, —NR$_{13}$-A$_1$R$_{14}$, aryl, cycloalkyl, heteroaryl, and heterocyclo;

A$_1$ is —(CH$_2$)$_r$—;

A$_2$ is —(CH$_2$)$_s$—;

$R_{13}$ and $R_{14}$ are selected from hydrogen, alkyl, substituted alkyl, aryl, cycloalkyl, heteroaryl, and heterocyclo, or when attached to the same nitrogen atom may form an optionally-substituted heteroaryl or heterocyclo ring; and r and s are selected from 0, 1, 2, 3, and 4.

Advantageously, in compounds of (I) herein, including formula (Ia), Y is —C(=O)NH—. Particularly, it is preferred that when $R_6$ is hydrogen, Y is —C(=O)NH— or a group other than —NHC(=O)—.

Advantageously, in compounds of (I) herein, including formula (Ia), B is selected from alkoxy, —$(CH_2)_n$—$C_{3-7}$ cycloalkyl, —$(CH_2)_n$-(heteroaryl or heterocyclo), and —$(CH_2)_n$-phenyl, wherein each $R_6$ is optionally substituted with one to two $R_7$, and/or in the case of a non-aromatic ring, a keto (=O) group; wherein $R_7$ is selected from $C_{1-6}$alkyl, substituted $C_{1-4}$alkyl, halogen, trifluoromethoxy, trifluoromethyl, cyano, hydroxy, $C_{1-4}$alkoxy, nitro, phenyl, benzyl, phenyloxy, benzyloxy, $NH_2$, $NH(C_{1-4}$alkyl), $N(C_{1-4}$alkyl)$_2$, cyclopentyl, cyclohexyl, or five or six membered heteroaryl or heterocycle; and n is 0, 1, 2 or 3, more preferably 0.

Advantageously, in compounds of (I) herein, including formula (Ia), $R_4$ is optionally-substituted aryl or heteroaryl, more preferably optionally substituted phenyl.

Advantageously, in compounds of (I) herein, including formula (Ia), $R_{5a}$ and $R_{5b}$ are independently selected from hydrogen, $C_{1-4}$alkyl, halogen, trifluoromethoxy, trifluoromethyl, hydroxy, $C_{1-4}$alkoxy, cyano, $NH_2$, $NH(C_{1-4}$alkyl), and $N(C_{1-4}$alkyl)$_2$. More preferably, $R_{5a}$ is halogen or lower alkyl, more preferably chloro or methyl, and $R_{5b}$ is hydrogen.

Advantageously, in compounds of (I) herein, including formula (Ia), $R_6$ is preferably not hydrogen. Preferred compounds are those where $R_6$ is alkyl, —O—$(CH_2)_r$—$R_{13}$, —$NR_{13}R_{14}$, morpholinyl, or diazepinyl, wherein $R_{13}$ and $R_{14}$ are selected from hydrogen, alkyl, hydroxyalkyl, cyanoalkyl, morpholinylalkyl, $C_{3-6}$cycloalkylalkyl, pyrrolidinylalkyl, piperidinylalkyl, or together form pyrrolidinyl or piperidinyl, wherein each $R_6$ group is optionally substituted with one to two groups selected from alkyl, substituted alkyl, halogen, lower alkoxy, amino, lower aminoalkyl, and lower alkylamino, and r is 0, 1, 2 or 3.

Also preferred are compounds of formula (Ib),

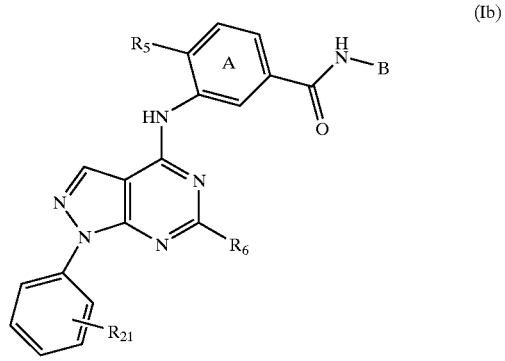

(Ib)

in which
B is selected from —$(CH_2)_n$—$C_{3-7}$cycloalkyl, —$(CH_2)_n$-(five to six membered heteroaryl or heterocyclo), and —$(CH_2)_n$-phenyl, wherein each $R_6$ is optionally substituted with one to two $R_7$, and in the case of a non-aromatic ring, in addition to one to two $R_7$, optionally a keto (=O) group;
$R_5$ is hydrogen, $C_{1-4}$alkyl, halogen, trifluoromethoxy, trifluoromethyl, hydroxy, $C_{1-4}$alkoxy, or cyano;

$R_6$ is (i) —O—$(CH_2)_r$—$R_{13}$ or —$NR_{13}$—$(CH_2)_s$—$R_{14}$, or (ii) alkyl, morpholinyl, or diazepinyl optionally substituted with one to two groups selected from alkyl, substituted alkyl, halogen, lower alkoxy, amino, and alkylamino;
$R_7$ and $R_2$, are independently selected from $C_{1-6}$alkyl, substituted $C_{1-4}$alkyl, halogen, trifluoromethoxy, trifluoromethyl, cyano, hydroxy, $C_{1-4}$alkoxy, nitro, phenyl, benzyl, phenyloxy, benzyloxy, $NH_2$, $NH(C_{1-4}$alkyl), $N(C_{1-4}$alkyl)$_2$, cyclopentyl, cyclohexyl, and five or six membered heteroaryl or heterocycle;
$R_{13}$ and $R_{14}$ are selected from hydrogen, alkyl, hydroxy, hydroxyalkyl, cyanoalkyl, morpholinyl, $C_{3-7}$cycloalkyl, pyrrolidinyl, piperidinyl, or together form pyrrolidinyl or piperidinyl;
r and s are is 0, 1, 2, or 3; and
n is 0, 1, or 2.

Utility

The compounds of the invention are selective inhibitors of p38 kinase activity, and in particular, isoforms p38α and p38β. Accordingly, compounds of formula (I) have utility in treating conditions associated with p38 kinase activity. Such conditions include diseases in which cytokine levels are modulated as a consequence of intracellular signaling via p38, and in particular, diseases that are associated with an overproduction of cytokines IL-1, IL-4, IL-8, and TNF-α. As used herein, the terms "treating" or "treatment" encompass either or both responsive and prophylaxis measures, e.g., measures designed to inhibit or delay the onset of the disease or disorder, achieve a full or partial reduction of the symptoms or disease state, and/or to alleviate, ameliorate, lessen, or cure the disease or disorder and/or its symptoms. When reference is made herein to inhibition of "p-38α/β kinase," this means that either p38α and/or p38β kinase are inhibited. Thus, reference to an $IC_{50}$ value for inhibiting p-38α/β kinase means that the compound has such effectiveness for inhibiting at least one of, or both of, p38α and p38β kinases.

In view of their activity as inhibitors of p-38α/β kinase, compounds of Formula (I) are useful in treating p-38 associated conditions including, but not limited to, inflammatory diseases, autoimmune diseases, destructive bone disorders, proliferative disorders, angiogenic disorders, infectious diseases, neurodegenerative diseases, and viral diseases.

More particularly, the specific conditions or diseases that may be treated with the inventive compounds include, without limitation, pancreatitis (acute or chronic), asthma, allergies, adult respiratory distress syndrome, chronic obstructive pulmonary disease, glomerulonephritis, rheumatoid arthritis, systemic lupus erythematosis, scleroderma, chronic thyroiditis, Grave's disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic β-cell disease; diseases characterized by massive neutrophil infiltration; rheumatoid spondylitis, gouty arthritis and other arthritic conditions, cerebral malaria, chronic pulmonary inflammatory disease, silicosis, pulmonary sarcoisosis, bone resorption disease, allograft rejections, fever and myalgias due to infection, cachexia secondary to infection, meloid formation, scar tissue formation, ulcerative colitis, pyresis, influenza, osteoporosis, osteoarthritis and multiple myeloma-related bone disorder, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovasculization, and infantile haemangiomas; viral diseases including acute hepatitis infection (including hepatitis A, hepatitis B and hepatitis C), HIV infection and CMV retinitis, AIDS, ARC or malignancy, and herpes; stroke, myocardial ischemia, ischemia in stroke heart attacks, organ hyposia, vascular hyperplasia, cardiac and renal reperfusion injury, thrombosis, cardiac hypertrophy, thrombin-induced platelet aggregation, endotoxemia and/or toxic shock syndrome, and conditions associated with prostaglandin endoperoxidase syndase-2.

In addition, p38 inhibitors of this invention inhibit the expression of inducible pro-inflammatory proteins such as prostaglandin endoperoxide synthase-2 (PGHS-2), also referred to as cyclooxygenase-2 (COX-2). Accordingly, additional p38-associated conditions include edema, analgesia, fever and pain, such as neuromuscular pain, headache, pain caused by cancer, dental pain and arthritis pain. The inventive compounds also may be used to treat veterinary viral infections, such as lentivirus infections, including, but not limited to equine infectious anemia virus; or retro virus infections, including feline immunodeficiency virus, bovine immunodeficiency virus, and canine immunodeficiency virus.

When the terms "p38 associated condition" or "p38 associated disease or disorder" are used herein, each is intended to encompass all of the conditions identified above as if repeated at length, as well as any other condition that is affected by p38 kinase activity.

The present invention thus provides methods for treating such conditions, comprising administering to a subject in need thereof an effective amount of at least one compound of Formula (I) or a salt thereof. The methods of treating p38 kinase-associated conditions may comprise administering compounds of Formula (I) alone or in combination with each other and/or other suitable therapeutic agents useful in treating such conditions.

"Other suitable therapeutic agents" encompasses, but is not limited to, an agent or agents selected from the group consisting of an immunosuppressant, anti-cancer agent, antiviral agent, anti-inflammatory agent, anti-fungal agent, antibiotic, anti-vascular hyperproliferation compound, anti-arrhythmic agent, phospodiesterase inhibitor, angiogenesis modulator, anti-proliferative agent, anti-tumor agent, and/or anti-infective agent. In the methods of the present invention, such other therapeutic agent(s) may be administered prior to, simultaneously with or following the administration of the compound(s) of the present invention.

Examples of suitable other anti-inflammatory agents with which the inventive compounds may be used include aspirin, non-steroidal antiinflammatory drugs (NSAIDs) (such as ibuprofen and naproxin), TNF-α inhibitors (such as tenidap and rapamycin or derivatives thereof), or TNF-α antagonists (e.g., infliximab, OR1384), prednisone, dexamethasone, Enbrel®, cyclooxygenase inhibitors (i.e., COX-1 and/or COX-2 inhibitors such as Naproxen®, Celebrex®, or Vioxx®), CTLA4-Ig agonists/antagonists, CD40 ligand antagonists, IMPDH inhibitors, such as mycophenolate (CellCept®), integrin antagonists, alpha-4 beta-7 integrin antagonists, cell adhesion inhibitors, interferon gamma antagonists, ICAM-1, prostaglandin synthesis inhibitors, budesonide, clofazimine, CNI-1493, CD4 antagonists (e.g., priliximab), other p38 mitogen-activated protein kinase inhibitors, protein tyrosine kinase (PTK) inhibitors, IKK inhibitors, therapies for the treatment of irritable bowel syndrome (e.g., Zelmac® and Maxi-K® openers such as those disclosed in U.S. Pat. No. 6,184,231 B1), or NF-κB inhibitors, such as corticosteroids, calphostin, CSAIDs, 4-substituted imidazo [1,2-A] quinoxalines as disclosed in U.S. Pat. No. 4,200,750; Interleukin-10, glucocorticoids, salicylates, nitric oxide, and other immunosuppressants; and nuclear translocation inhibitors, such as deoxyspergualin (DSG).

Examples of suitable antibiotics with which the inventive compounds may be used include cyclosporins (e.g., cyclosporin A), CTLA4-Ig, antibodies such as anti-ICAM-3, anti-IL-2 receptor (Anti-Tac), anti-CD45RB, anti-CD2, anti-CD3 (OKT-3), anti-CD4, anti-CD80, anti-CD86, monoclonal antibody OKT3, agents blocking the interaction between CD40 and CD154 (a.k.a. "gp39"), such as antibodies specific for CD40 and/or CD 154, fusion proteins constructed from CD40 and/or CD154/gp39 (e.g., CD401 g and CD8gp39), β-lactams (e.g., penicillins, cephalosporins and carbopenams); β-lactam and lactamase inhibitors (e.g., augamentin); aminoglycosides (e.g., tobramycin and streptomycin); macrolides (e.g., erythromycin and azithromycin); quinolones (e.g., cipro and tequin); peptides and deptopeptides (e.g. vancomycin, synercid and daptomycin) metabolite-based anti-biotics (e.g., sulfonamides and trimethoprim); polyring systems (e.g., tetracyclins and rifampins); protein synthesis inhibitors (e.g., zyvox, chlorophenicol, clindamycin, etc.); and nitro-class antibiotics (e.g., nitrofurans and nitroimidazoles).

Examples of suitable antifungal agents with which the inventive compounds may be used include fungal cell wall inhibitors (e.g., candidas), azoles (e.g., fluoconazole and vericonazole), and membrane disruptors (e.g., amphotericin B).

Examples of suitable antiviral agents for use with the inventive compounds include nucleoside-based inhibitors, protease-based inhibitors, viral-assembly inhibitors, and other antiviral agents such as abacavir.

Other additional therapeutic agents with which the inventive compounds may be used include antioxidants and/or lipid peroxidation inhibitors such as probucol, BO-653, Vitamin A, Vitamin E, and AGI-1067; antiosteoporosis agents such as alendronate and raloxifene; anviral agents for such as nucleoside-based inhibitors, protease-based inhibitors, and viral-assembly inhibitors; anti-osteoporosis agents such as alendronate, risedronate, PTH, PTH fragment, raloxifene, calcitonin, RANK ligand antagonists, calcium sensing receptor antagonists, TRAP inhibitors, selective estrogen receptor modulators (SERM) and AP-1 inhibitors; steriodal or non-steroidal progesterone receptor agonists ("PRA"), such as levonorgestrel, medroxyprogesterone acetate (MPA); phosphodiesterase (PDE) inhibitors that block the hydrolysis cAMP and/or cGMP including dipyridamole, cilostazol, sildenafil, rolipram, denbutyline, theophylline (1,2-dimethylxanthine), and ARIFLO™ (i.e., cis-4-cyano-4-[3-(cyclopentyloxy)-4-methoxyphenyl] cyclohexane-1-carboxylic acid), or PDE inhibitors in combination with anti-platelet agents; anticancer strategies and chemotherapies such as taxol and/or cisplatin; and antitumor agents such as paclitaxel, adriamycin, epithilones, cisplatin, and carboplatin.

The above other therapeutic agents, when employed in combination with the compounds of the present invention, may be used, for example, in those amounts indicated in the Physicians' Desk Reference (PDR) or as otherwise determined by one of ordinary skill in the art. In the methods of the present invention, such other therapeutic agent(s) may be administered prior to, simultaneously with, or following the administration of the inventive compounds.

The present invention also provides pharmaceutical compositions capable of treating p38-kinase associated conditions, including TNF-α, IL-1, and/or IL-8 mediated conditions, as described above. The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

The compounds of Formula (T) may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrasternal injection or infusion techniques (e.g., as sterile injectable aq. or non-aq. solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as PLASTIBASE® (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CAR-BOPOL 934®). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The effective amount of a compound of the present invention may be determined by one of ordinary skill in the art, and includes exemplary dosage amounts for a mammal of from about 0.05 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species, that are affected by mediation of p38 enzyme levels.

Compounds of formula (I), including the compounds described in the examples hereof, have been tested in one or more of the assays described below and have shown activity as inhibitors of p38α/β enzymes and TNF-α.

Biological Assays

Generation of p38 Kinases cDNAs of human p38α, β and γ isozymes were cloned by PCR. These cDNAs were subcloned in the pGEX expression vector (Pharmacia). GST-p38 fusion protein was expressed in *E. Coli* and purified from bacterial pellets by affinity chromatography using glutathione agarose. p38 fusion protein was activated by incubating with constitutively active MKK6. Active p38 was separated from MKK6 by affinity chromatography. Constitutively active MKK6 was generated according to Raingeaud et al. [*Mol. Cell. Biol.*, 1247–1255 (1996)].

TNF-α Production by LPS-Stimulated PBMCs

Heparinized human whole blood was obtained from healthy volunteers. Peripheral blood mononuclear cells (PBMCs) were purified from human whole blood by Ficoll-Hypaque density gradient centrifugation and resuspended at a concentration of $5\times10^6$/ml in assay medium (RPMI medium containing 10% fetal bovine serum). 50 ul of cell suspension was incubated with 50 ul of test compound (4× concentration in assay medium containing 0.2% DMSO) in 96-well tissue culture plates for 5 minutes at RT. 100 ul of LPS (200 ng/ml stock) was then added to the cell suspension and the plate was incubated for 6 hours at 37° C. Following incubation, the culture medium was collected and stored at −20° C. TNF-α concentration in the medium was quantified using a standard ELISA kit (Pharmingen-San Diego, Calif.). Concentrations of TNF-α and $IC_{50}$ values for test compounds (concentration of compound that inhibited LPS-stimulated TNF-α production by 50%) were calculated by linear regression analysis.

p38 Assay

The assays were performed in V-bottomed 96-well plates. The final assay volume was 60 μl prepared from three 20 μl additions of enzyme, substrates (MBP and ATP) and test compounds in assay buffer (50 mM Tris pH 7.5, 10 mM $MgCl_2$, 50 mM NaCl and 1 mM DTT). Bacterially expressed, activated p38 was pre-incubated with test compounds for 10 min. prior to initiation of reaction with substrates. The reaction was incubated at 25° C. for 45 min. and terminated by adding 5 μl of 0.5 M EDTA to each sample. The reaction mixture was aspirated onto a pre-wet filtermat using a Skatron Micro96 Cell Harvester (Skatron, Inc.), then washed with PBS. The filtermat was then dried in a microwave oven for 1 min., treated with MeltilLex A scintillation wax (Wallac), and counted on a Microbeta scintillation counter Model 1450 (Wallac). Inhibition data were analyzed by nonlinear least-squares regression using Prizm (GraphPadSoftware). The final concentration of reagents in the assays are ATP, 1 μM; [γ-$^{33}$P]ATP, 3 nM; MBP (Sigma, #M1891), 2 μg/well; p38, 10 nM; and DMSO, 0.3%.

TNF-α Production by LPS-Stimulated Mice

Mice (Balb/c female, 6–8 weeks of age, Harlan Labs; n=8/treatment group) were injected intraperitoneally with 50 ug/kg lipopolysaccharide (LPS; *E. coli* strain 0111:B4, Sigma) suspended in sterile saline. Ninety minutes later, mice were sedated by $CO_2$:$O_2$ inhalation and a blood sample was obtained. Serum was separated and analyzed for TNF-alpha concentrations by commercial ELISA assay per the manufacturer's instructions (R&D Systems, Minneapolis, Minn.).

Test compounds were administered orally at various times before LPS injection. The compounds were dosed either as suspensions or as solutions in various vehicles or solubilizing agents.

Abbreviations

For ease of reference, the following abbreviations are employed herein, including the methods of preparation and Examples that follow:

Ph=phenyl
Bz=benzyl
t-Bu=tertiary butyl
Me=methyl
Et=ethyl
Pr=propyl
Iso-P=isopropyl
MeOH=methanol
EtOH=ethanol
EtOAc=ethyl acetate
Boc=tert-butyloxycarbonyl
DCM=dichloromethane
DCE=1,2-dichloroethane
DMF=dimethyl formamide
DMSO=dimethyl sulfoxide
TFA=trifluoroacetic acid
THF=tetrahydrofuran
HATU=O-(7-Azabenzotriazol-t-yl-N,N,N',N'-tetramethyluronim hexafluorophosphate
KOH=potassium hydroxide
$K_2CO_3$=potassium carbonate
$POCl_3$=phosphorous oxychloride
EDC or EDCI=1-(3-Dimethylaminopropyl)-3-ethylcarbodiimide hydrochloride
DIPEA=diisopropylethylamine
HOBt=1-hydroxybenzotriazole hydrate
m-CPBA=m-chloroperbenzoic acid
NaH=sodium hydride
NaOH=sodium hydroxide
Pd=palladium
Pd/C=palladium on carbon
min=minute(s)
L=liter
mL=milliliter
L=microliter
g=gram(s)
mg=milligram(s)
mol=moles
mmol=millimole(s)
meq=milliequivalent
RT or rt=room temperature
ret. t.=HPLC retention time (minutes)
sat or sat'd=saturated
aq.=aqueous
TLC=thin layer chromatography
HPLC=high performance liquid chromatography
RP HPLC=reverse phase HPLC
LC/MS=high performance liquid chromatography/mass spectrometry
MS=mass spectrometry
NMR=nuclear magnetic resonance
mp=melting point Methods of Preparation Compounds of formula I may generally be prepared according to the following schemes and the knowledge of one skilled in the art, and/or the methods described in U.S. Pat. No. 6,670,357, and/or U.S. patent application Ser. No. 09/573,829, both assigned to the present assignee and incorporated herein by reference. In the schemes, the groups B, $R_3$–$R_6$, and m are as described herein for compounds of Formula (I).

Scheme 1

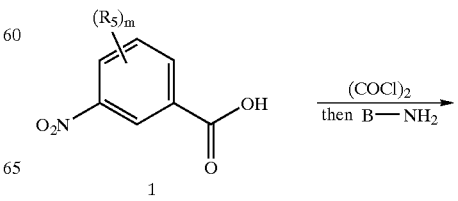

1

-continued

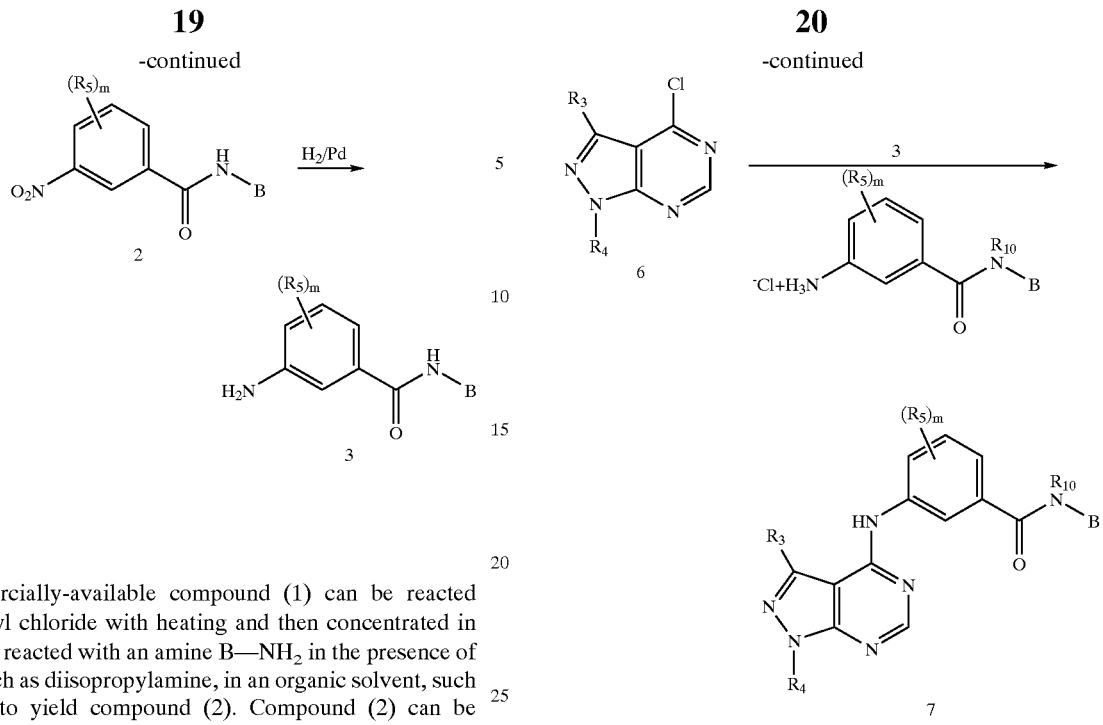

Commercially-available compound (1) can be reacted with oxalyl chloride with heating and then concentrated in vacuo and reacted with an amine B—NH$_2$ in the presence of a base, such as diisopropylamine, in an organic solvent, such as DCM to yield compound (2). Compound (2) can be reacted with hydrogen in the presence of a catalyst, such as Pd, in an alcoholic solvent, such as EtOH, at rt to afford compound (3). Compound (3) can then be used as in Scheme 2 to produce compounds (7) of Scheme 2.

Scheme 2

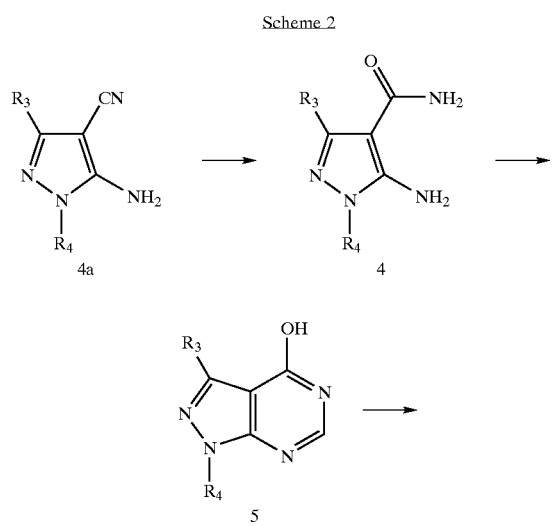

Pyrazole (4a) prepared according to the procedure described in the literature (*J. Org. Chem.*, Vol. 21, at p. 1240, [1956]) can be treated with conc. sulfuric acid at 0° C. to ambient temperature to produce compound (4). Reacting compound (4) in formamide at an elevated temperature produces compound (5) which can be reacted with POCl$_3$ in to produce compound (6). Compound (6) can be reacted with compound (3) at elevated temperature to produce compound (7).

Compound (3) can be prepared by 1) reacting commercially-available 4-amino-3-methylbenzoic acid and N-(tert-butoxycarbonyl)anhydride in THF to produce a Boc-protected aniline intermediate; 2) reacting the aniline intermediate with -(3-dimethylaminopropyl)-3-ethylcarbodiimide hydrochloride, HOBt, and DMF, followed by addition of methoxyamine hydrochloride and DIPEA to produce a BOC-protected N-methoxyamide intermediate; and 3) reacting that methoxyamide intermediate in a solution of HCl in dioxane to produce compound (3) as a hydrochloride salt. Alternatively, compound (3) can be prepared as shown in Scheme 1.

Scheme 3

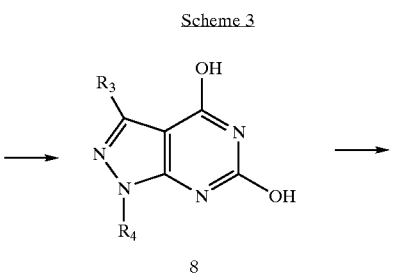

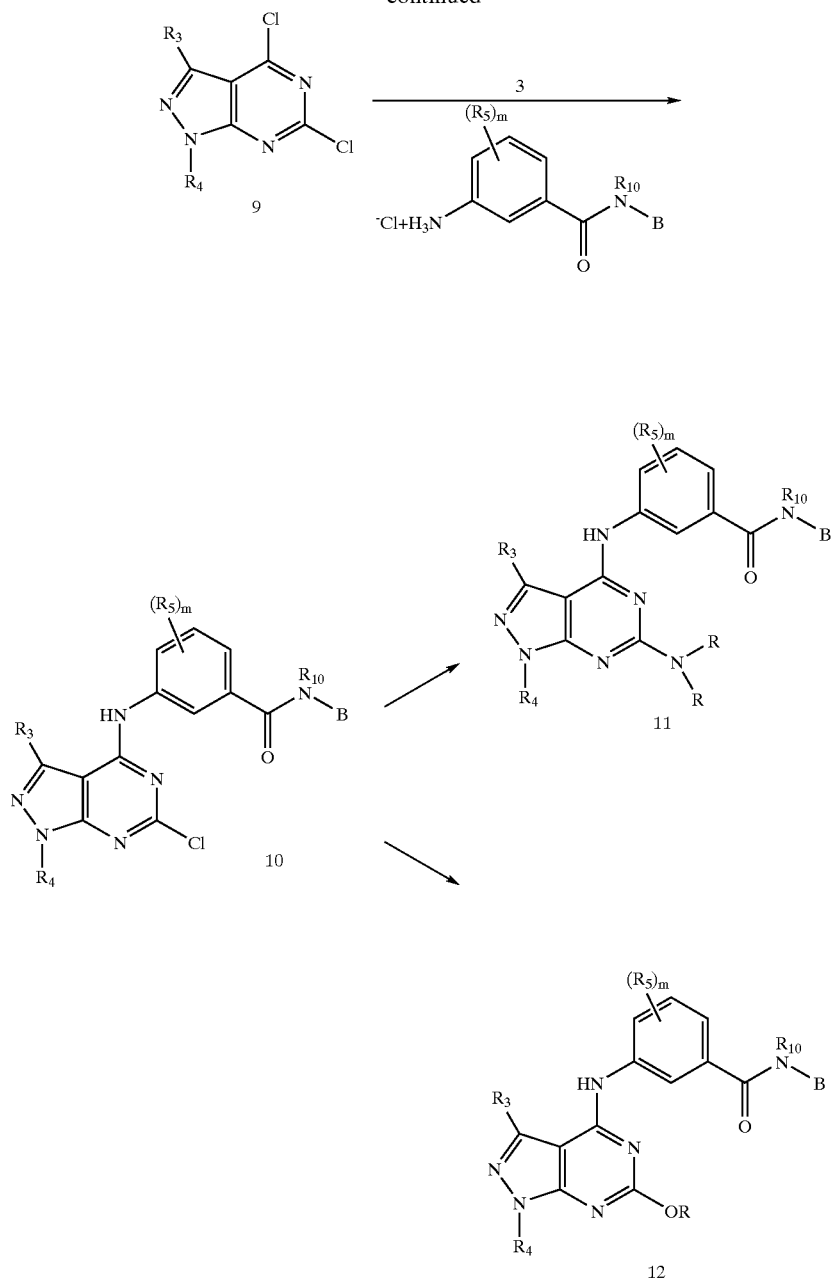

Pyrazole (4) can be reacted with urea at an elevated temperature to produce compound (8) which can be reacted with POCl₃ in presence or absence of PCl₅ to produce compound (9). Compound (9) can be reacted with compound (3) at elevated temperature to produce compound (10). Compound (10) can be reacted with an amine RRNH at elevated temperature in presence or absence of an organic solvent to produce compound (11). Alternatively, compound (10) can be treated with an alcohol ROH in presence of a base such as sodium or potassium alkoxide, sodium or potassium bistrimethylsilazide or sodium hydride at elevated temperature to produce (12). Preparation of compounds (11) and (12) can be carried out under microwave conditions using identical conditions.

Scheme 4

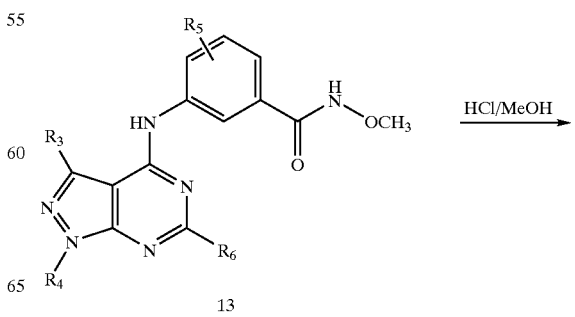

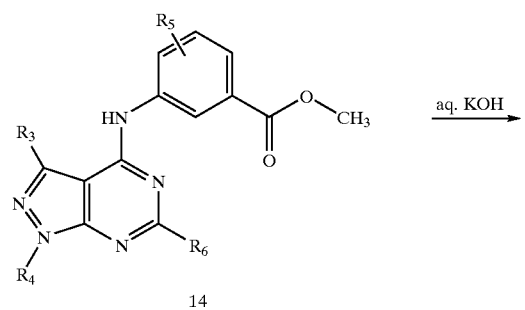

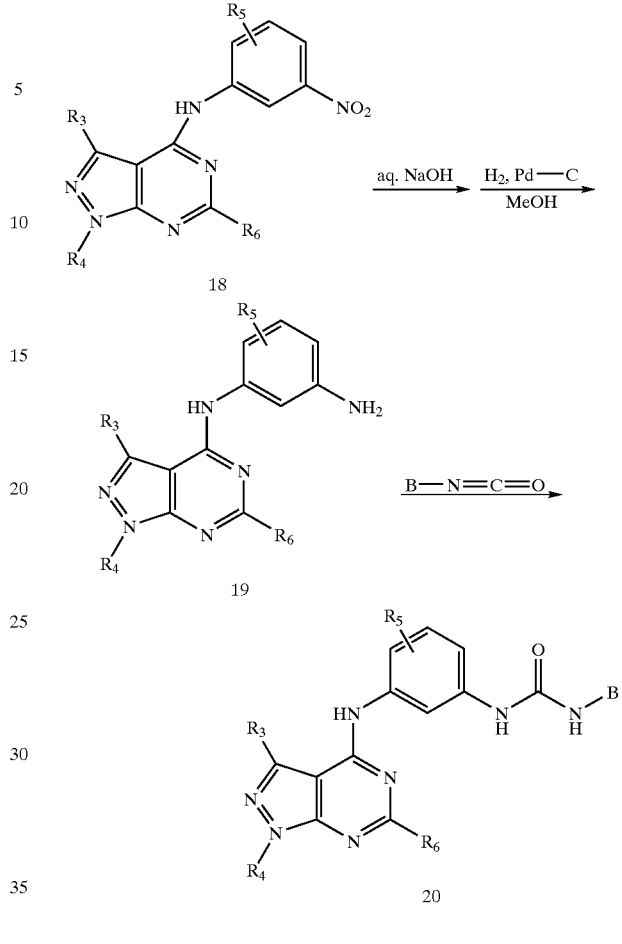

A substituted hydroxamate (13) can be reacted with acid, such as HCl, in anhydrous MeOH, to afford compound (14). Compound (14) can be reacted with an aq. base such KOH with heating to form compound (15). Compound (15) is reacted with an amine B—$NH_2$ in the presence of a coupling reagent, such as HATU, and a base such as diisopropylamine, in an organic solvent, such as N-methylpyrrolidinone to afford compounds (16). Hydroxamate (13) can be prepared as outlined in Scheme 1 and/or as shown in U.S. patent application Ser. No. 10/036,293.

Chloropyrazolopyrimidine (6a) (see Schemes 2 and 3) can be reacted with an aniline (17) (e.g., see Scheme 3) in anhydrous DMF at rt to afford compound (18). Reaction of compound (18) can be reacted with hydrogen in the presence of a catalyst, such as Pd/C, in an organic solvent, such as MeOH to afford compound (19). Reaction of compound (19) with an isocyanate in an organic solvent, such as DCE affords compound (20). Methods of making compounds (6a) wherein $R_6$ is other than hydrogen are well known in the field, e.g., such compounds may be made from compounds (9) as described in Scheme 3, or following procedures known in the field and/or set forth in the literature.

Scheme 5

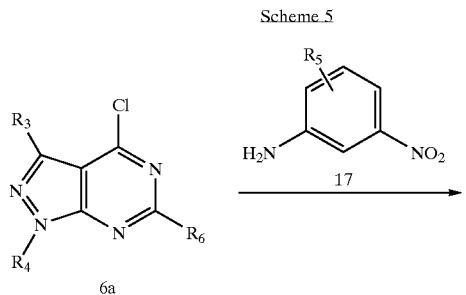

Scheme 6

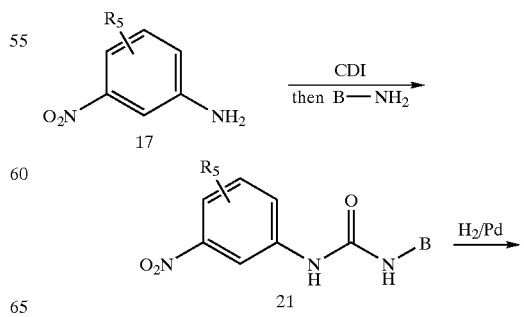

25
-continued

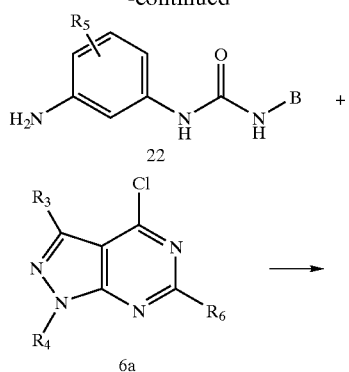

26
-continued

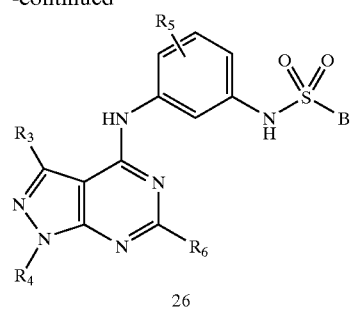

Commercially-available compound (17) can be reacted with a sulfonyl chloride in the presence of a base, such as TEA, in an organic solvent, such as DCM to yield compound (24). Reaction of compound (24) with hydrogen in the presence of a catalyst, such as Pd in a solvent, such as MeOH, yields compound (25). Reaction of compound (25) with chloride (6a) in an organic solvent, such as DMF, at rt affords compound (26).

In addition, other compounds of formula I may be prepared using procedures generally known to those skilled in the art and/or set forth in the various patent applications and publications cited herein, which are incorporated herein by reference. As an illustration, the following examples provide additional methods for the preparation of the compounds of this invention.

The invention will now be further described by the following working examples, which are preferred embodiments of the invention. These examples are illustrative rather than limiting. There may be other embodiments that fall within the spirit and scope of the invention as defined by the appended claims.

Commercially-available compound (17), can be reacted with carbonyl diimidazole and an amine B—$NH_2$ in an organic solvent, such as DCE, to yield compound (21). Reaction of compound (21) with hydrogen in the presence of a catalyst, such as Pd, in an alcoholic solvent such as EtOH affords compound (22). Reaction of (22) with chloride (6) in an organic solvent, such as DMF, affords compound (23).

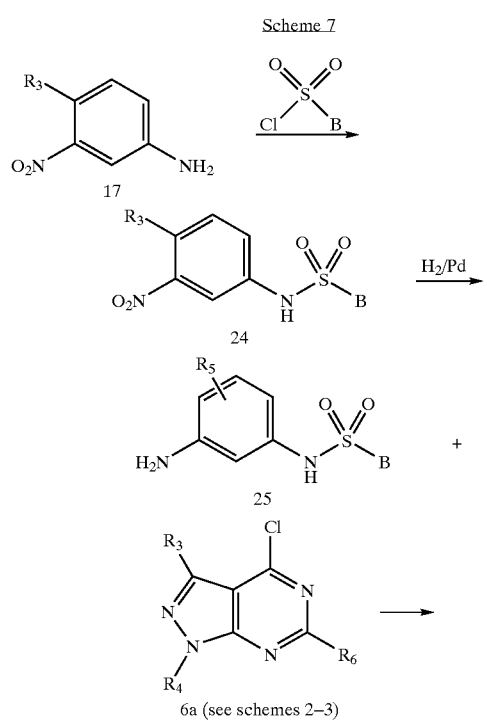

EXAMPLE 1

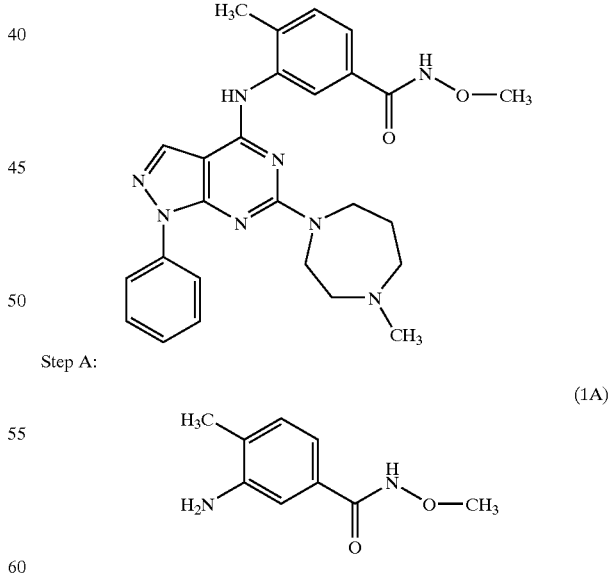

Step A:

A mixture of commercially-available 4-amino-3-methylbenzoic acid (100 g, 0.66 mol) and N-(tert-butoxycarbonyl)anhydride (150 g, 0.68 mol) in THF (1000 mL) was slowly heated to 50° C. overnight. The resulting mixture was cooled to rt and the solvent removed on a rotary evaporator. The resulting solids were triturated with hexanes and dried in vacuo to afford 151 g (91%) of the crude BOC-protected aniline intermediate as a light pink solid.

To the above aniline intermediate was added EDCI (127 g, 0.66 mol), HOBt (90 g, 0.66 mol), and DMF (1000 ml), and the resulting mixture was stirred at rt for 30 minutes followed by addition of methoxyamine hydrochloride (55 g, 0.66 mol) in one portion. After stirring for 10 min, the mixture was cooled using an ice bath. DIPEA (250 ml, 1.4 mol) was added at a rate so as to maintain the internal reaction temperature below 25° C. After the addition was complete, the ice bath was removed and the reaction was stirred overnight at rt. The reaction mixture was partitioned between 0.5 L of water and 1.5 L of EtOAc and the resulting layers were separated. The aqueous portion was extracted with additional EtOAc (400 mL×3), and the combined organic extracts were washed with water (300 mL×3), cold 0.5 N aq. HCl (400 mL×2), and water (500 mL). The product was then extracted with cold 0.5 N aq. NaOH (300 mL×3) and the combined basic aqueous extracts were neutralized to pH=8 by a slow addition of cold 0.5 N aq. HCl. The resulting solid which precipitated was collected by filtration and washed with cold water. The wet solid was decolorized in hot EtOH with active charcoal to give 106 g of white solid as the BOC-protected N-methoxyamide intermediate.

To a slurry of the above solid (91 g, 0.32 mol) in 1,4-dioxane (400 mL) at rt was added a 4M solution of HCl in dioxane (400 mL), and the resulting mixture was stirred at rt overnight. Diethyl ether (1000 mL) was added and the precipitated solid was collected by filtration and triturated with a hot EtOH/H$_2$O mixture (4:1 v/v). Drying the resulting solid in vacuo afforded 53 g of the hydrochloride salt of compound 1A as a white solid. $^1$H NMR (d$_6$-DMSO): δ9.5–9.9 (br. s, 1H), 7.75 (s, 1H), 7.55 (d, 1H), 7.36 (d, 1H), 3.70 (s, 3H), 2.38 (s, 3H).

Step B:

(1B)

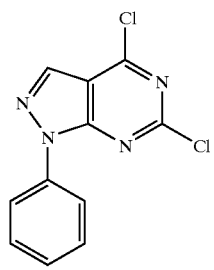

A solution of 4,6-dihydroxy-1-phenyl-pyrazolo-[3,4-d] pyrimidine (600 mg, 2.63 mmol) (see *J. Org. Chem.*, Vol. 23, 1958, at p. 852) and phosphorus pentachloride (2.5 g) in phosphorus oxychloride (25 mL) was heated under reflux for 3 h. The solution was concentrated under reduced pressure. The residue was diluted with minimum volume of DCM and poured into crushed ice. The mixture was extracted with DCM (25 mL, 2×), dried (MgSO$_4$), filtered, and concentrated to obtain 4,6-dichloro-1-phenyl-pyrazolo-[3,4-d] pyrimidine (compound 1B, 648 mg, 93%) as a yellow solid.

Step C:

(1C)

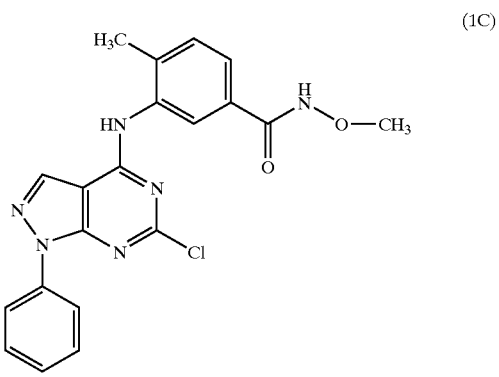

A solution of compound 1B (132 mg, 0.5 mmol), compound 1A (108 mg, 0.5 mmol), and diisopropylethyl amine (420 μL, 3 mmol) in absolute EtOH (20 mL) was heated to 60° C. for 4 h. The solution was cooled to rt and concentrated. The residue was diluted with DCM (50 mL), washed with 1 N aq. HCl solution (20 mL, 2×), dried (MgSO$_4$), filtered, and concentrated. The residue was triturated with ether-hexanes mixture (20 mL, 3:1) and the solid was filtered, washed with ether-hexanes mixture (3:1), and dried in vacuo to obtain the titled compound 1C (122 mg, 60%) as a yellow solid. HPLC Retention time=4.13 min; LC/MS (M+H)$^+$=409.21.

Step D: Example 1

A solution of compound 1C (81 mg, 0.2 mmol), and N-methylhomopiperazine (57 mg, 0.5 mmol) in isopropanol (1 mL) was heated to 100° C. for 3 h. The mixture was cooled to rt and concentrated. The residue was chromatographed on a preparative reversed phase HPLC column: YMC 30×100 mm, 10 min gradient with 5 min hold, flow rate 20 mL/min, detection wave length 220 nm, starting solvent: 90% solvent A (10% MeOH-90% H2O-0.1% CF$_3$COOH) and 10% solvent B(90% MeOH-10% H2O-0.1% CF$_3$COOH); final solvent: 90% solvent B and 10% solvent A. Fraction containing the product was concentrated in SpeedVac. The residue was diluted with DCM and concentrated under reduced pressure and in vacuo to obtain Example 1 (78 mg, 65%) as a yellow solid. HPLC Retention time=2.60 min.; LC/MS (M+H)$^+$=487.00.

EXAMPLE 2

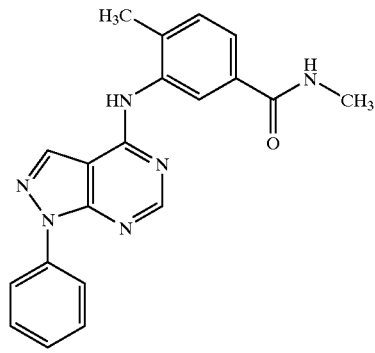

Step A:

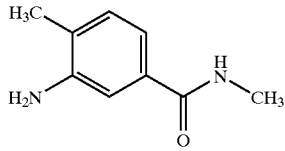
(2A)

A solution of 3-amino-4-methylbenzoic acid (5.0 g, 33.1 mmol), EDC (12.7 g, 66.2 mmol), N-hydroxybenzotriazole (5.37 g, 39.72 mmol), a 2 M solution of methyl amine in THF (66 mL, 132.3 mmol), and diisopropylethyl amine (22.7 mL, 132.4 mmol) in THF (85 mL) and DMF (15 mL) was stirred at 54° C. for 2 h. The mixture was concentrated under reduced pressure in vacuo, and the residue was purified by chromatography on a silica gel column. Elution with 20% EtOAc in hexanes, followed by EtOAc, and 2% MeOH in EtOAc afforded compound 2A as a cream-colored solid (5.14 g, 95%). HPLC Retention time=0.356 min.; LC/MS $(M+H)^+=165.2$.

Step B:

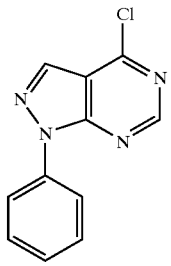
(2B)

A suspension of 4-hydroxy-1-phenyl-pyrazolo[3,4-d] pyrimidine (1.1 g, 5 mmol) (J. Org. Chem., Vol. 21, at p. 1240, [1956]) in phosphorus oxychloride (20 mL) was heated to 90° C. for 3 h. The solution was cooled to rt and concentrated. The residue was diluted with DCM (5 mL) and poured into crushed ice. The mixture was extracted with DCM (30 mL, 2x), dried (MgSO$_4$), filtered, and concentrated under reduced pressure, in vacuo to obtain compound 2B as a white solid (975 mg, 85%). HPLC Retention time=2.957 min; LC/MS $(M+H)^+=231.00$.

Step C: Example 2

A mixture of compound 2B (115 mg, 0.5 mmol) and compound 2A (164 mg, 1 mmol) in minimal volume of MeOH was heated to 140° C. for 1 h in an open round bottom flask. The mixture was cooled to rt and the solid was stirred with 1 N aq. HCl solution (25 mL) for 1 h. The solid was filtered, washed with water (5 mL, 5x), ether (5 mL, 5x), and dried in vacuo at 50° C. to obtain Example 2 (165 mg, 84%) as a white solid. HPLC Retention time=2.74 min; LC/MS $(M+H)^+=359.29$.

EXAMPLE 3

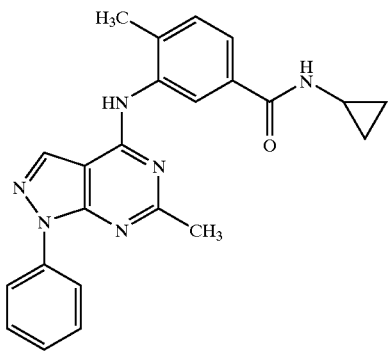

Step A:

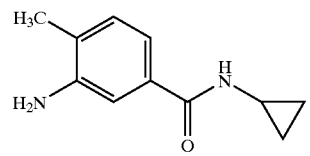
(3A)

A solution of 3-amino-4-methylbenzoic acid (5.0 g, 33.1 mmol), EDC (12.65 g, 66 mmol), N-hydroxybenzotriazole (5.35 g, 39.6 mmol), cyclopropyl amine (9.1 mL, 132 mmol), and diisopropylethyl amine (22.3,mL, 132 mmol) in THF (85 mL) and DMF (15 mL) was stirred at 54° C. for 110 min. The mixture was concentrated under reduced pressure and in vacuo and the residue was purified by chromatography on a silica gel column. Elution with 5% EtOAc in hexanes, followed by 1% MeOH in EtOAc and EtOAc-MeOH—NH$_4$OH mixture (98:1:1) afforded compound 3A as a light pink solid (6.34 g, 100%). HPLC Retention time=0.56 min.; LC/MS $(M+H)^+=191.02$.

Step B:

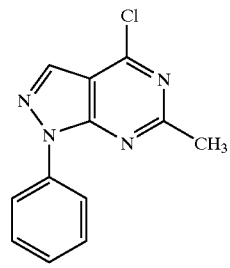
(3B)

A suspension of 4-hydroxy-6-methyl-1-phenyl-pyrazolo-[3,4-d]pyrimidine (350 mg, 1.55 mmol) (Ind. J. Chem. 31B, 163, 1992) in phosphorus oxychloride (10 mL) was heated under to 90–95° C. for 9 h. The mixture was cooled to rt and concentrated. The residue was slowly poured into crushed ice. The precipitated solid was filtered, washed with water, and dried in air to obtain 4-chloro-6-methyl-1-phenyl-pyrazolo-[3,4-d]pyrimidine (compound 3B, 335 mg, 89%) as an off-white solid. HPLC Retention time=3.70 min.; LC/MS $(M+H)^+=245.13$.

Step C: Example 3

A suspension of compound 3B (73 mg, 0.3 mmol) and compound 3A (95 mg, 0.5 mmol) in MeOH (5 mL) was heated to 130° C. for 1 h in an open round bottom flask. The mixture was cooled to rt, diluted with MeOH (10 mL) and stirred for 10 min. The precipitated solid was filtered, washed with MeOH (5 mL, 2×), ether (5 mL, 4×) and dried in vacuo to obtain Example 3 (47 mg, 36%) as a white solid. HPLC Retention time=2.90 min; LC/MS (M+H)$^+$=399.32.

EXAMPLE 4

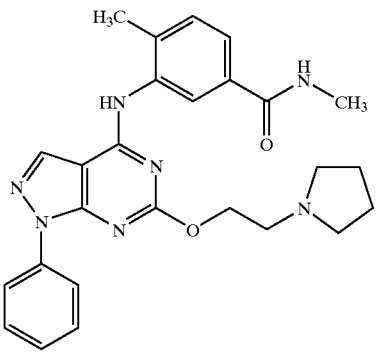

Step A:

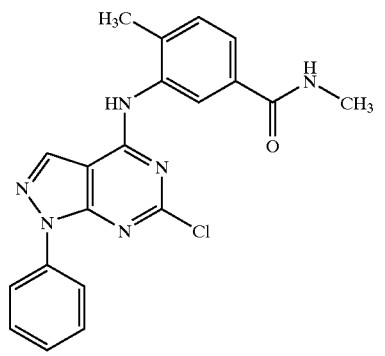

(4A)

A solution of compound 1B (480 mg, 1.81 mmol), compound 2A (320 mg, 1.99 mmol), and diisopropylethyl amine (930 µL, 5.43 mmol) in absolute EtOH (36 mL) was heated to 62° C. for 9.5 h. The solution was cooled to rt and concentrated. The residue was diluted with water, sonicated for several min and the solid was filtered, washed with water, and dried in vacuo to obtain a pale yellow solid which was triturated with ether-EtOAc mixture (9:1) to obtain compound 4A (273 mg) as pale yellow solid. A second crop was obtained by trituration of the filtrate with ether for a combined yield of 397 mg (56%). HPLC Retention time=4.08 min; LC/MS (M+H)$^+$=393.43.

Step B: Example 4

A solution of compound 4A (40 mg, 0.10 mmol), 2-hydroxyethylpyrrolidine (120 µL, 1 mmol), and 1 M solution of sodium hexamethyldisilazide in THF (0.5 mL, 0.5 mmol) in DMF (2 mL) was heated to 165° C. under microwave conditions for 30 min. The mixture was cooled to rt and quenched with a 4 N HCl solution in dioxane (0.5 mL) and concentrated. The residue was purified on a preparative reversed phase HPLC column: YMC S5 ODS 30×250 mm, 30 min gradient, flow rate 25 mL/min, detection wave length 220 nm, starting solvent: 80% solvent A (10% MeOH-90% H2O-0.1% CF$_3$COOH) and 20% solvent B(90% MeOH-10% H2O-0.1% CF$_3$COOH); final solvent: 100% solvent B. Fraction containing the product was concentrated in SpeedVac to obtain compound 4 (41 mg, 70%) as a tan solid. HPLC Retention time=3.00 min; LC/MS (M+H)$^+$=472.54.

EXAMPLES 5–46

Compounds in Examples 5–46 were prepared following the same or similar procedure described above for Examples 1–4.

TABLE 1

| Ex. # | Structure | (M + H)$^+$ | HPLC Retention time (min) |
|---|---|---|---|
| 5 | 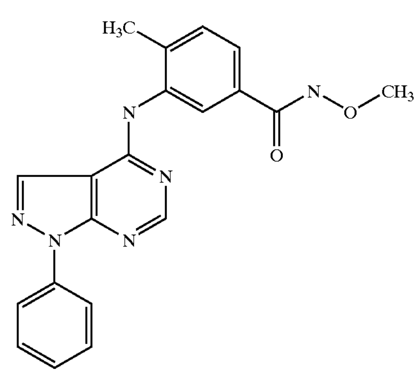 | 375.26 | 2.78$^a$ |

TABLE 1-continued

| Ex. # | Structure | (M + H)+ | HPLC Retention time (min) |
|---|---|---|---|
| 6 | 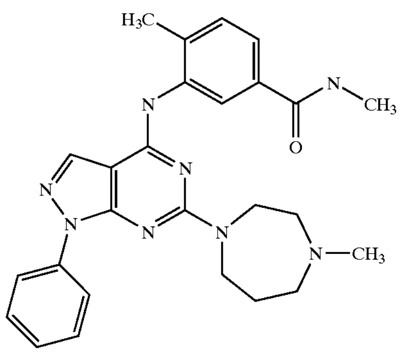 | 471.29 | 3.27[a] |
| 7 | 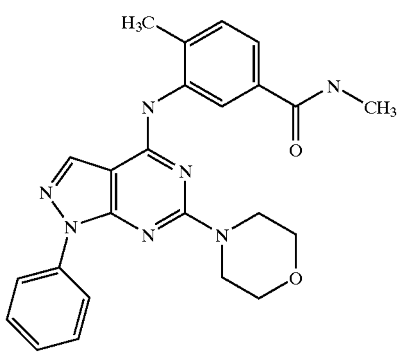 | 444.28 | 4.22[a] |
| 8 | 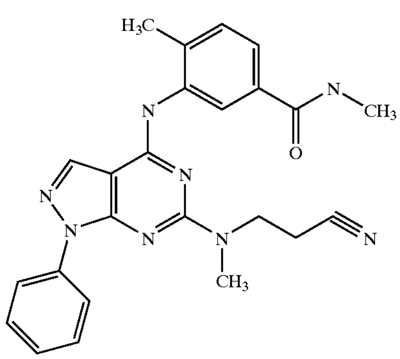 | 441.26 | 4.10[a] |
| 9 | 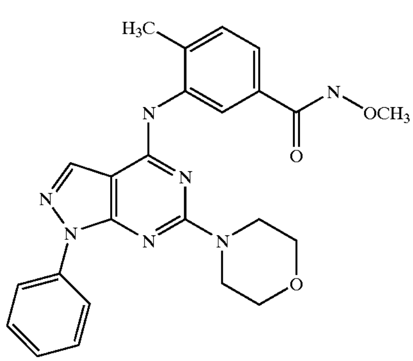 | 460.31 | 4.22[a] |

TABLE 1-continued

| Ex. # | Structure | (M + H)⁺ | HPLC Retention time (min) |
|---|---|---|---|
| 10 | 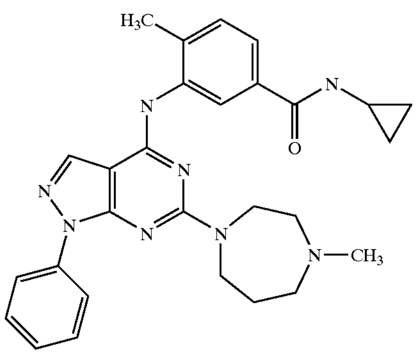 | 497.23 | 3.39[a] |
| 11 | 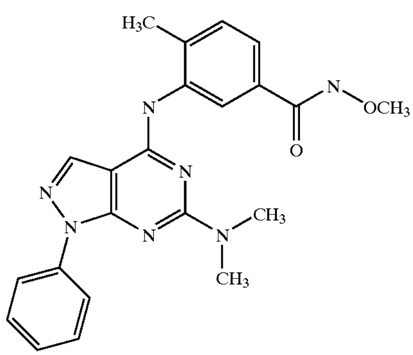 | 418.45 | 4.27[a] |
| 12 | 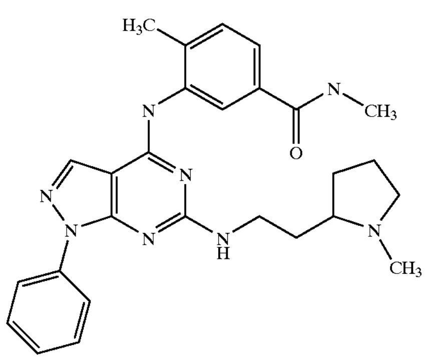 | 485.31 | 2.85[a] |
| 13 | 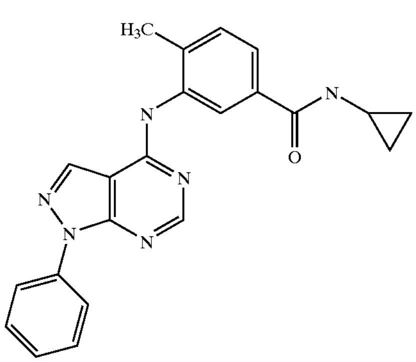 | 385.35 | 3.00[a] |

TABLE 1-continued

| Ex. # | Structure | (M + H)+ | HPLC Retention time (min) |
|---|---|---|---|
| 14 | 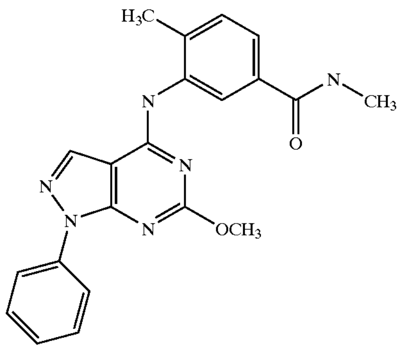 | 389.24 | 4.00[a] |
| 15 | 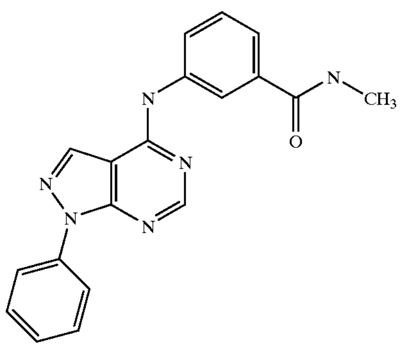 | 345.20 | 3.73[a] |
| 16 | 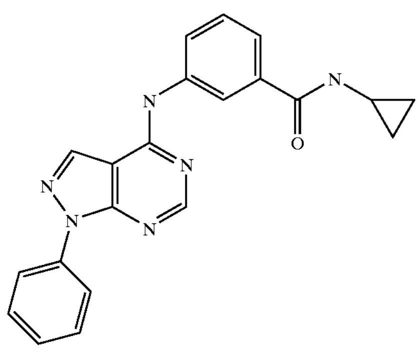 | 371.22 | 3.96[a] |
| 17 | 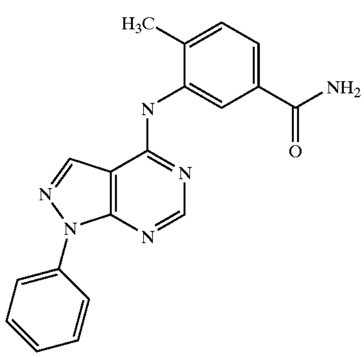 | 345.4 | 3.38[a] |

TABLE 1-continued

| Ex. # | Structure | (M + H)+ | HPLC Retention time (min) |
|---|---|---|---|
| 18 | 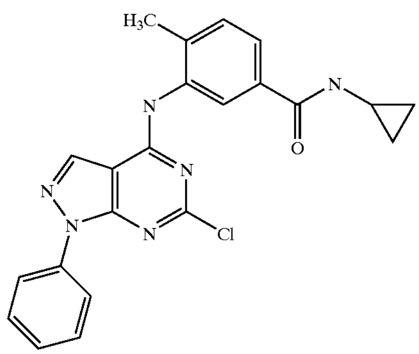 | 419.35 | 3.61[a] |
| 19 | 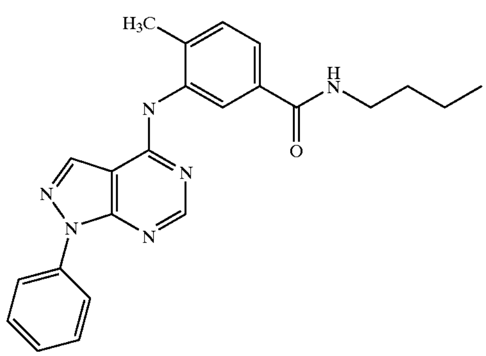 | 401.5 | 4.08[a] |
| 20 | 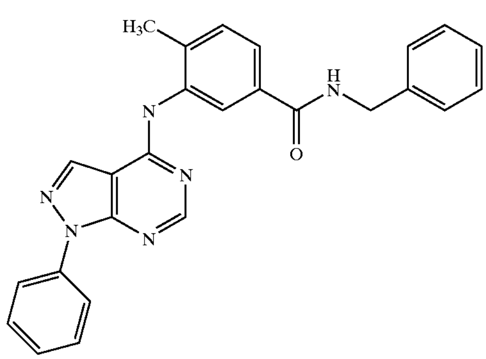 | 435.44 | 4.12[a] |
| 21 | 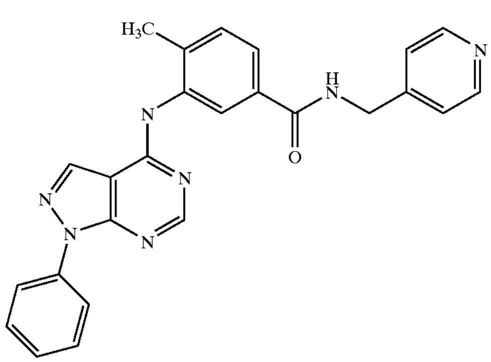 | 422.46 | 3.20[a] |

TABLE 1-continued

| Ex. # | Structure | (M + H)+ | HPLC Retention time (min) |
|---|---|---|---|
| 22 | 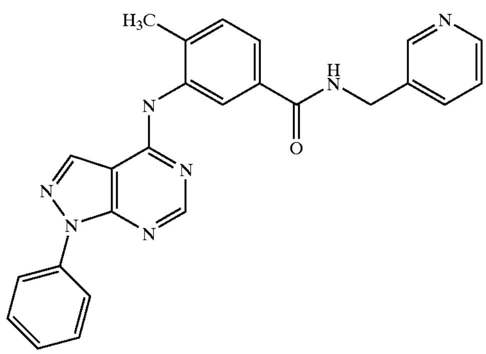 | 422.42 | 3.25[a] |
| 23 | 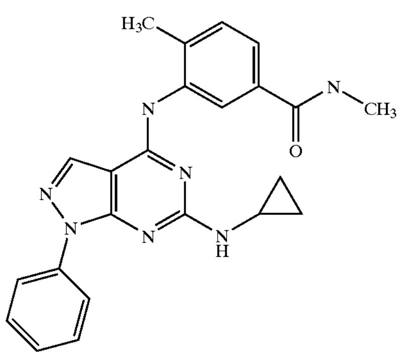 | 414.55 | 3.75[a] |
| 24 | 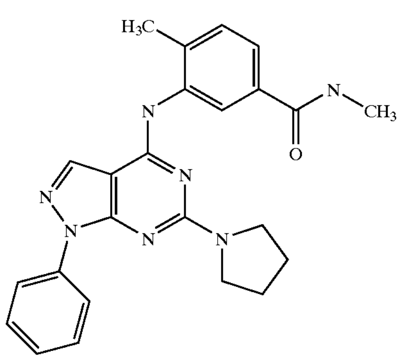 | 428.49 | 4.29[a] |
| 25 | 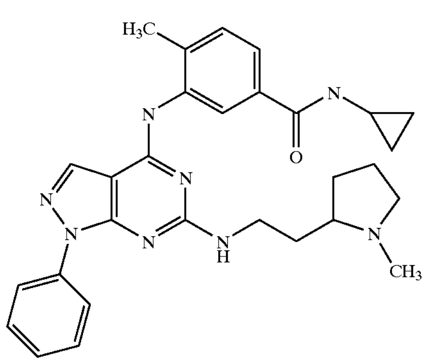 | 511.63 | 2.94[a] |

TABLE 1-continued

| Ex. # | Structure | (M + H)+ | HPLC Retention time (min) |
|---|---|---|---|
| 26 | 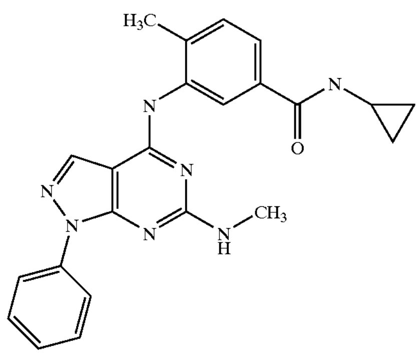 | 414.53 | 3.54[a] |
| 27 | 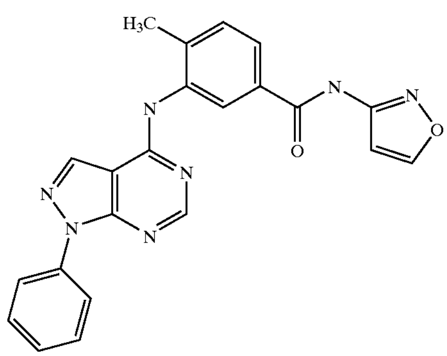 | 412.45 | 3.77[a] |
| 28 | 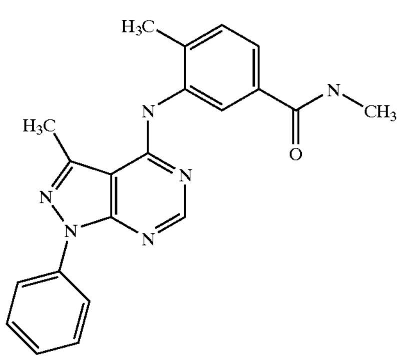 | 373.46 | 2.93[a] |
| 29 | 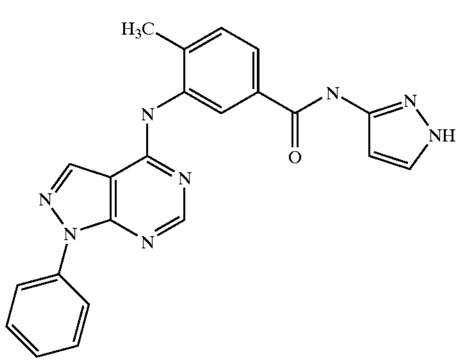 | 411.48 | 3.57[a] |

TABLE 1-continued

| Ex. # | Structure | (M + H)+ | HPLC Retention time (min) |
|---|---|---|---|
| 30 | 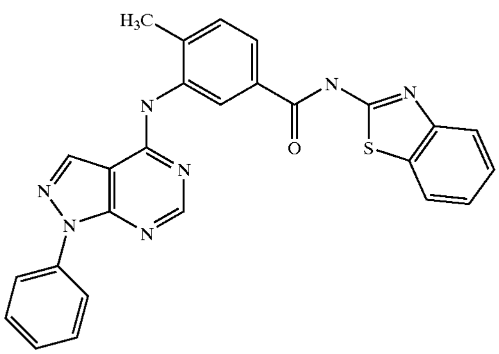 | 478.48 | 4.56[a] |
| 31 | 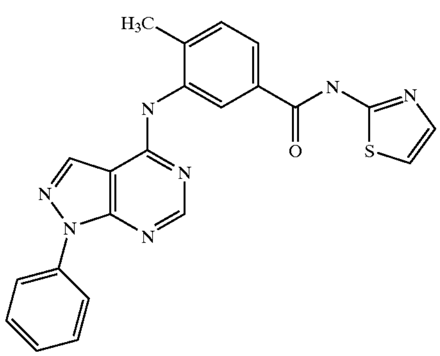 | 428.39 | 3.96[a] |
| 32 | 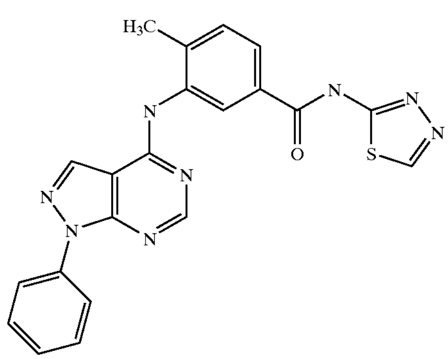 | 429.43 | 3.81[a] |
| 33 | 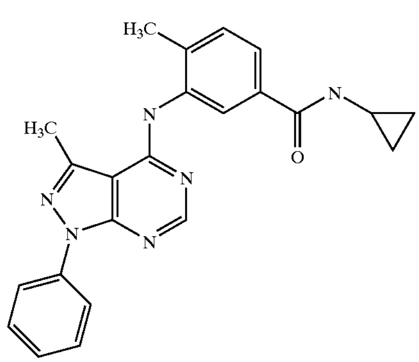 | 399.52 | 3.12[a] |

TABLE 1-continued

| Ex. # | Structure | (M + H)+ | HPLC Retention time (min) |
|---|---|---|---|
| 34 | 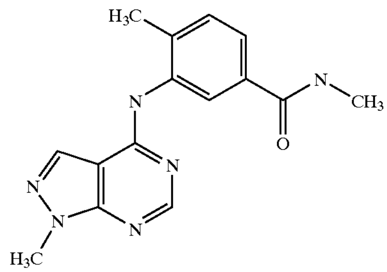 | 297.40 | 1.27[a] |
| 35 | 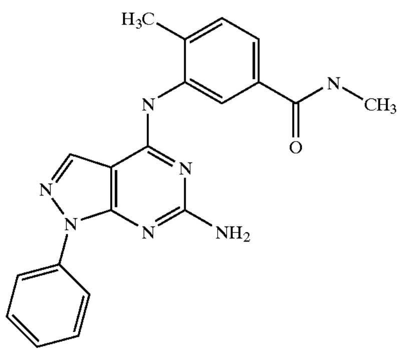 | 374.44 | 2.88[a] |
| 36 | 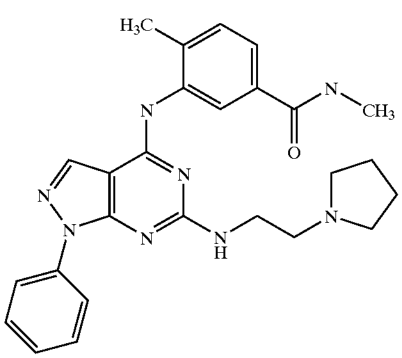 | 471.64 | 2.82[a] |
| 37 | 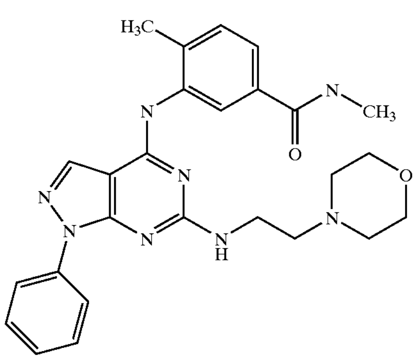 | 487.53 | 2.72[a] |

TABLE 1-continued

| Ex. # | Structure | (M + H)+ | HPLC Retention time (min) |
|---|---|---|---|
| 38 | 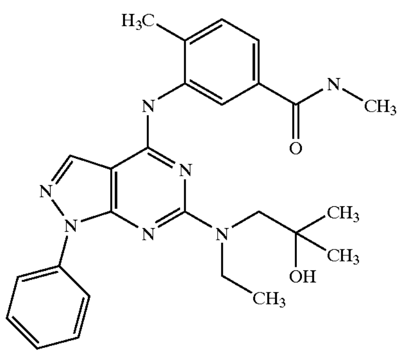 | 474.52 | 4.19[a] |
| 39 | 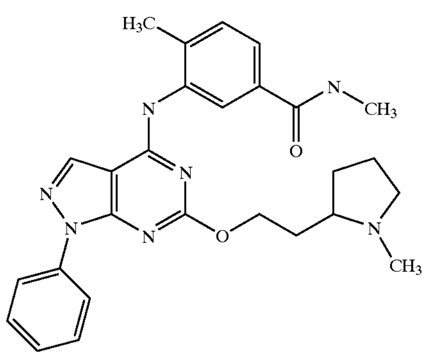 | 486.56 | 3.14[a] |
| 40 | 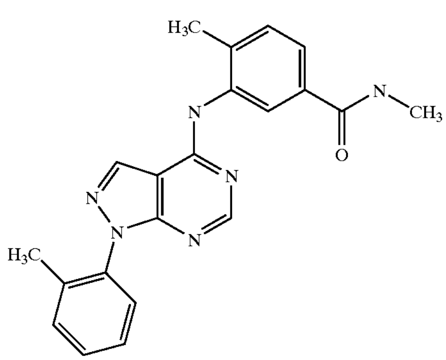 | 373.31 | 2.49[a] |
| 41 | 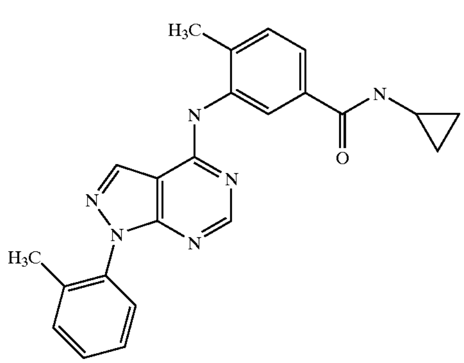 | 399.35 | 2.73[a] |

TABLE 1-continued

| Ex. # | Structure | (M + H)⁺ | HPLC Retention time (min) |
|---|---|---|---|
| 42 | 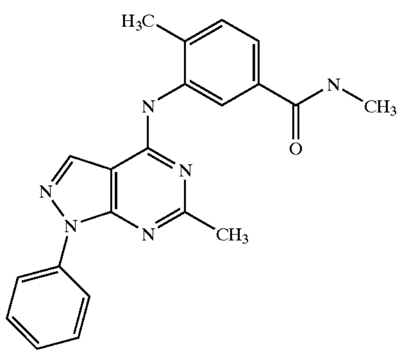 | 373.26 | 2.65[a] |
| 43 | 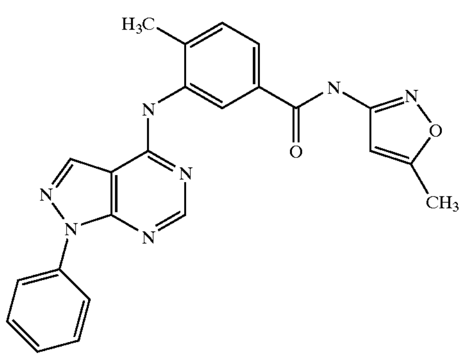 | 426.26 | 3.92[a] |
| 44 | 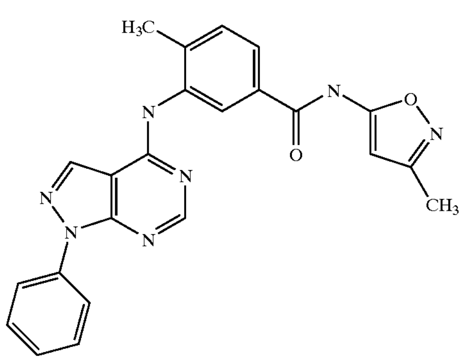 | 426.32 | 4.00[a] |
| 45 | 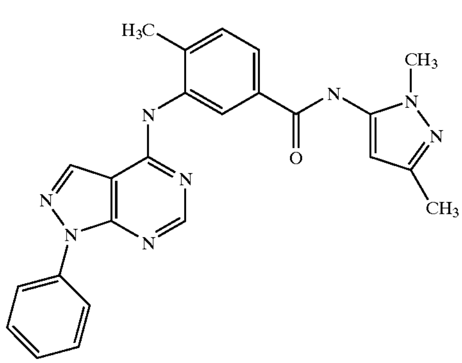 | 439.40 | 3.74[a] |

TABLE 1-continued

| Ex. # | Structure | (M + H)⁺ | HPLC Retention time (min) |
|---|---|---|---|
| 46 | 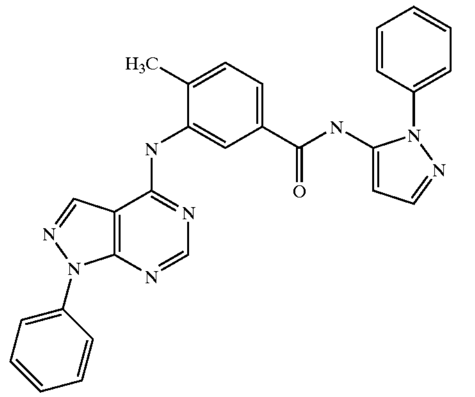 | 487.46 | 3.92ᵃ |

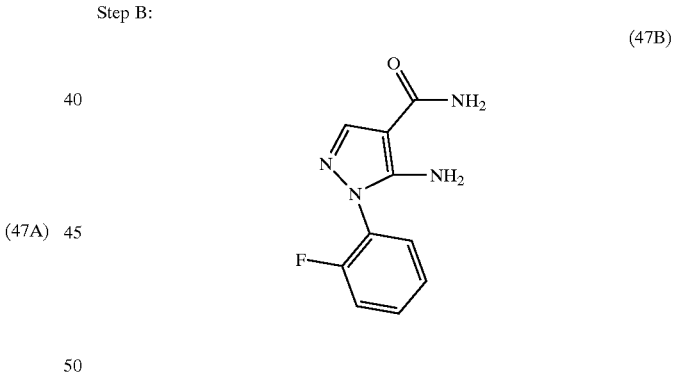

EXAMPLE 47

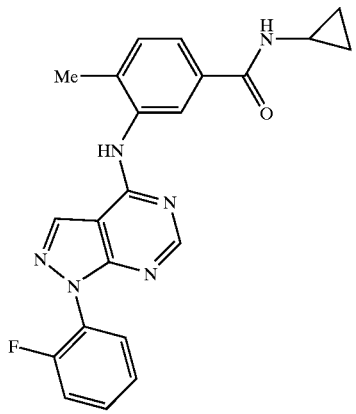

Step A:

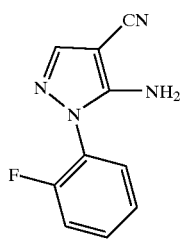

(47A)

Triethyl amine (6.67 g, 66 mmol) was added dropwise to a stirred suspension of 2-fluorophenylhydrazine hydrochloride (10.73 g, 66 mmol) in absolute ethanol (200 mL). After 10 min ethoxylidenemalononitrile (8.05 g, 66 mmol) was added in portions over a period of 30 min. The solution was stirred at rt overnight. An identical reaction at the same scale was run concurrently. Both reactions were combined and concentrated. The residue was diluted with dichloromethane (200 mL) and washed with 1 N aq. HCl solution (100 mL, 2×). The aq. layers were combined, extracted with dichloromethane (100 mL, 2×). Dichloromethane extracts were combined, washed with brine (100 mL, 2×), dried (MgSO₄), filtered, and concentrated under reduced and in vacuo. The residue was diluted with ether (50 mL) and the soild was filtered, washed with ether:hexanes (40 mL, 1:1) to obtain 1 (19 g, HPLC purity 90%) which was stirred with ether:hexanes mixture (200 mL, 1:4) for 16 h to obtain the title compound 47A (17.84 g, 67% yield). HPLC retention time: 0.89 min; LC/MS: 202.94 (M+H)⁺.

Step B:

(47B)

Cyanopyrazole 47A (17.84 g, 88.3 mmol) was added in portions to stirred conc. sulfuric acid (86 mL) immersed in an ice-water bath, over a period of 1 h. The cooling bath was removed and the solution was stirred at rt for 2.5 h. The sulfuric acid solution was carefully poured into crushed ice and neutralized with conc. aq. ammonium hydroxide solution. Temperature was maintained at 0–5° C. during neutralization. The precipitated solid was filtered, washed several times with water and dried. The solid was washed with ether several times and dried in vacuo to obtain the title compound 47B (160.06 g, 80% yield, pale yellow solid, HPLC purity: 98.7%). HPLC retention time: 0.70 min; LC/MS: 221.02 (M+H)⁺.

Step C:

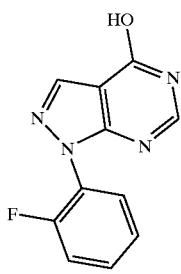

(47C)

A solution of compound 47B (12 g, 54.5 mmol) in formamide (218 mL) was heated to 191° C. (oil-bath temp.) for 3 h. The solution was cooled to rt and diluted with water (880 mL). The mixture was cooled in the refrigerator overnight. The solid was filtered, washed several times with water and dried in vacuo over phosphorus pentoxide to obtain the tite compound 47C (9.14 g, 73% yield, tan brown powder, HPLC purity: 100%). HPLC retention time: 0.96 min; LC/MS: 231.02 (M+H)$^+$.

Step D:

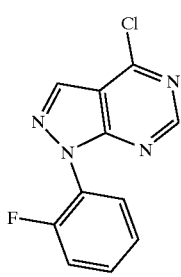

(47D)

A solution of compound 47C (8.93 g, 38.8 mmol) in phosphorus oxychloride (148 mL) was heated to 95° C. (oil-bath temp.) for 16 h. The solution was cooled to rt and most of phosphorus oxychloride was removed by distillation in vacuo. The residue was cooled in an ice-water bath and diluted with dichloromethane (107 mL). The dichloromethane solution was then slowly poured into a stirred mixture of satd. aq. sodium bicarbonate solution (491 mL) and dichloromethane (268 mL) at 0–5° C. The dichloromethane layer was separated and the aq. layer was extracted with dichloromethane (100 mL). The dichloromethane extracts were combined, washed with brine, dried (Na$_2$SO$_4$), filtered and concentrated under reduced pressure and in vacuo to obtain the title compound 47D (9.22 g, 96% yield, HPLC purity: 98%) as a light tan solid. HPLC retention time: 1.24 min; LC/MS: 248.98 (M+H)$^+$.

Step E:

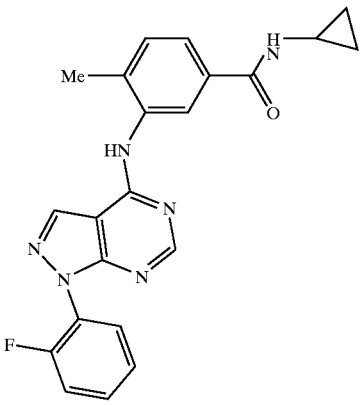

(47)

A solution of compound 47D (6 g, 24.1 mmol) and compound 3A (5.98 g, 31.4 mmol, free base) in dimethylformamide (54 mL) was heated to 78° C. (oil-bath temp.) for 110 min. The solution was cooled to rt and most of dimethylformamide was removed by distillation in vacuo. The residue was diluted with dichloromethane/methanol mixture (250 mL, 19:1) and 1 N aq. HCl solution and brine (60 mL, 2:1).The dichloromethane layer was separated and the aq. layer was extracted with dichloromethane (60 mL). The dichloromethane extracts were combined, washed with 1 N aq. HCl solution and brine (60 mL, 2:1), brine, dried (Na$_2$SO$_4$), filtered and concentrated under reduced pressure and in vacuo to obtain a tan solid which was suspended in ether/EtOAC mixture (9:1) and stirred overnight. The solid was filtered, suspened in satd. sodium bicarbonate solution, sonicated for few min and stirred. The solid was filtered, washed with water and dried in vacuo to obtain an off-white solid (8.72 g). Crystallization from i-PrOH/MeOH mixture afforded a white crystalline solid (4.44 g, HPLC purity 98.7%). Recrystallization of the filtrate from i-PrOH/MeOH mixture afforded additional compound of lower purity (97.6%). A suspension of compound 47 (8.38 g, HPLC purity: 98.7%) in i-PrOH (42 mL) and conc. HCl (2.1 mL) was sonicated and heated with stirring until a cloudy solution was formed. The solution was cooled to rt and stirred for 16 h. The crystalline solid was filtered, washed with isopropanol and dried in vacuo to obtain compound 47 (HCl salt) as a white solid (8.93 g) which was suspended in satd. aq. NaHCO$_3$ solution (50 mL), sonicated for 10 min and filtered. The solid was washed with water several times and dried in vacuo to obtain the title compound 47 (7.54 g) as a free base (HPLC purity: 98.96%).

EXAMPLE 48

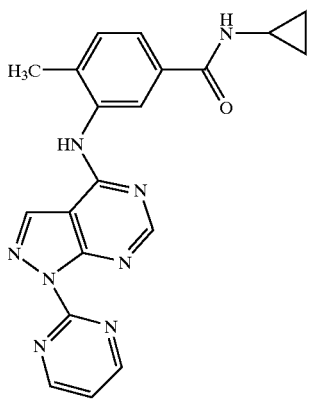

Step A:

(48A)

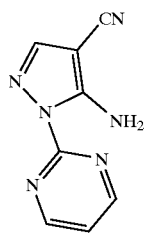

Ethoxylidenemalononitrile (3.2 g, 26.2 mmol) was added in portions over a period of 10 min. to a suspension of 2-hydrazinopyrimidine (2.87 g, 26 mmol) in absolute ethanol (13 mL). The mixture was stirred at rt overnight. The precipitated solid was filtered, washed with hexanes and dried in vacuo to obtain the title compound 48A (4.06 g, 84% yield).

Step B:

(48B)

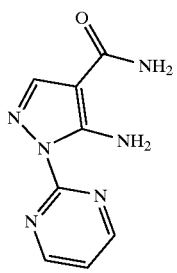

Cyanopyrazole 48A (4.06 g, 21.8 mmol) was added in portions to stirred conc. sulfuric acid (19 mL) immersed in an ice-water bath, over a period of 40 min. The cooling bath was removed and the solution was stirred at rt for 1 h. The sulfuric acid solution was carefully poured into crushed ice and neutralized with conc. aq. ammonium hydroxide solution. Temperature was maintained at 0–5° C. during neutralization. The precipitated solid was filtered, washed several times with water and dried in vacuo over $P_2O_5$ to obtain the title compound 48B (4.45 g, quantitative yield) as a light tan powder.

Step C:

(48C)

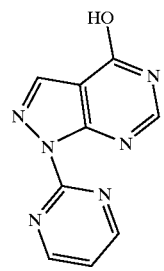

A solution of compound 48B (1.02 g, 4.99 mmol) and glacial acetic acid (0.36 mL) in triethylorthoformate (56.1 mL) was heated to 60° C. (oil-bath temp.) for 1 h. The solution was cooled to rt and concentrated under reduced pressure and in vacuo. The residue was diluted with ether and stirred for 16 h. The solid was filtered, washed several times with ether and dried in vacuo to obtain the title compound 48C (796 mg, 74% yield) as a pale yellow powder.

Step D:

(48D)

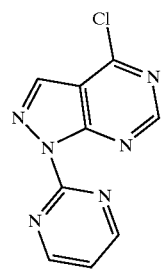

A suspension of compound 48C (350 mg, 1.63 mmol) in phosphorus oxychloride (6.3 mL) was heated to 93° C. (oil-bath temp.) for 20 h. The suspension was briefly heated to 114° C. to obtain a homogeneous solution which was cooled to rt and most of phosphorus oxychloride was removed by distillation in vacuo. The residue was poured into crushed ice and extracted with chloroform (27 mL, 3×). The organic extracts were combined, washed with water, dried ($Na_2SO_4$), filtered, and concentrated under reduced pressure and in vacuo to obtain the title compound 48D (270 mg, 71% yield) as a pale yellow solid.

Step E:

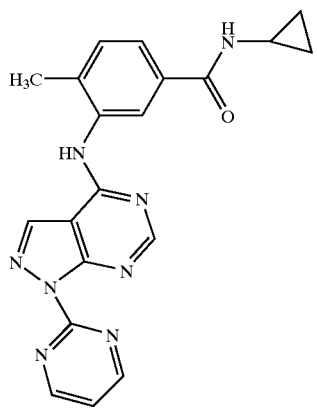

(48)

A suspension of compound 48D (35 mg, 0.15 mmol) and compound 3A (51.4 mg, 0.27 mmol, free base) in absolute ethanol (0.8 mL) was heated to 142° C. (oil-bath temp.) for 9 min. The solution was cooled to rt and purified by reverse phase chromatography on an automated preparative HPLC column: YMC 20×100 mm; Flow rate: 20 mL/min; Gradient time 10 min with 5 min hold; Wave length 220 nm; Starting solvent: 100% solvent A (10% MeOH-90% $H_2O$-0.1% TFA); Final solvent: solvent B (90% MeOH-10% $H_2O$-0.1% TFA). The fraction containing the product was concentrated under Speed Vac™ to obtain the title compound 48 (59 mg, 79% yield, white solid) as a trifluoroacetic acid salt.

EXAMPLES 49–107

Compounds in Examples 49–107 were prepared following the procedure described above for Examples 1–48.

TABLE 2

| Ex. # | Structure | $(M + H)^+$ | HPLC Retention time (min) |
|---|---|---|---|
| 49 | 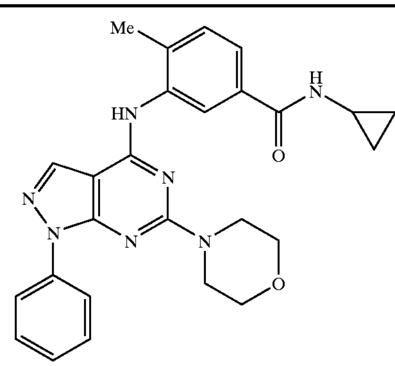 | 470.29 | 1.87[a] |
| 50 | 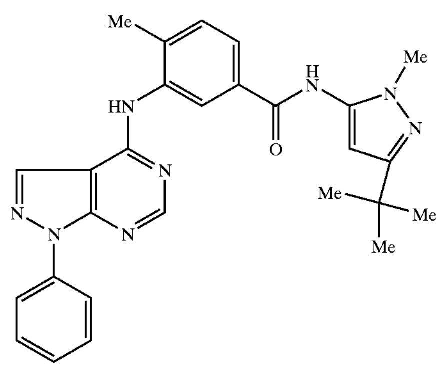 | 481.46 | 1.81[a] |
| 51 | 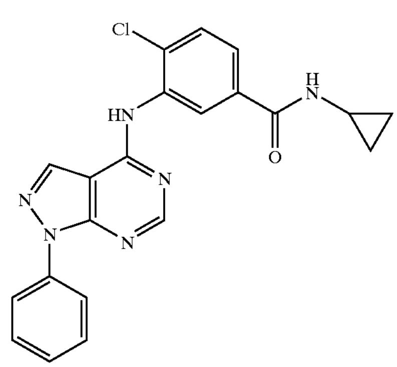 | 405.20 | 1.66[a] |

TABLE 2-continued

| Ex. # | Structure | (M + H)+ | HPLC Retention time (min) |
|---|---|---|---|
| 52 | 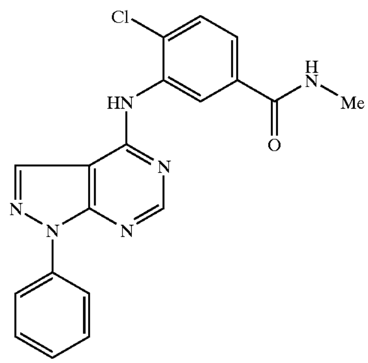 | 379.29 | 1.57[a] |
| 53 | 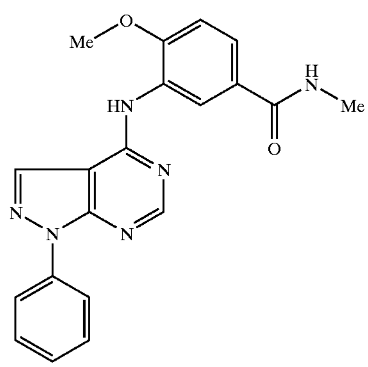 | 375.27 | 1.37[a] |
| 54 | 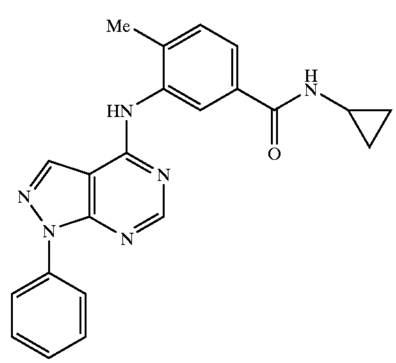 | 401.32 | 1.47[a] |
| 55 | 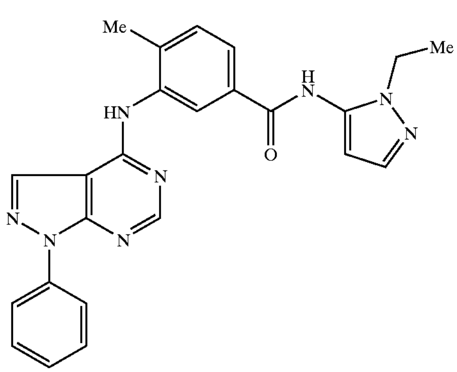 | 439.46 | 1.57[a] |

TABLE 2-continued

| Ex. # | Structure | (M + H)+ | HPLC Retention time (min) |
|---|---|---|---|
| 56 | 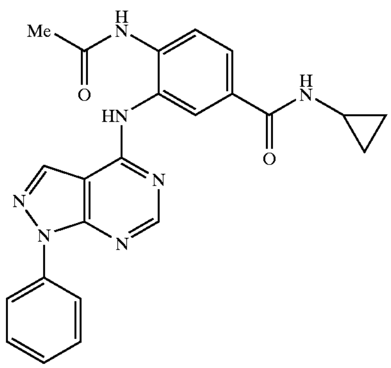 | 428.34 | 1.42[a] |
| 57 | 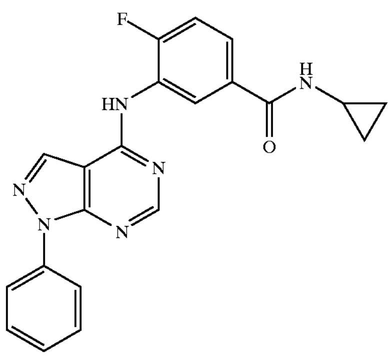 | 389.49 | 1.69[a] |
| 58 | 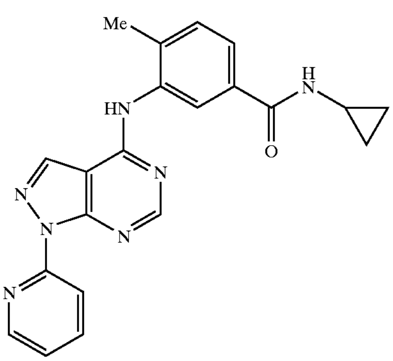 | 386.34 | 2.01[a] |
| 59 | 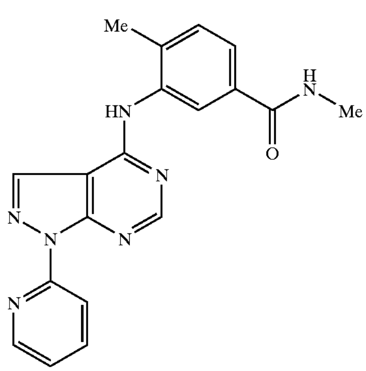 | 360.25 | 1.81[a] |

TABLE 2-continued

| Ex. # | Structure | (M + H)+ | HPLC Retention time (min) |
|---|---|---|---|
| 60 | 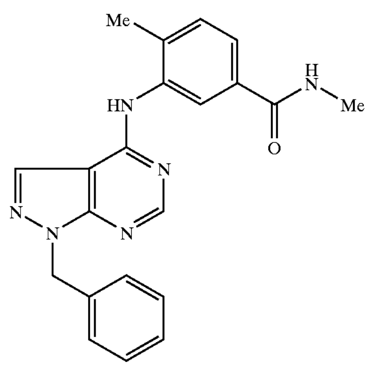 | 373.30 | 2.28[a] |
| 61 | 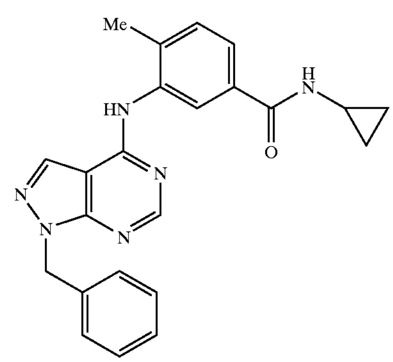 | 399.36 | 2.46[a] |
| 62 | 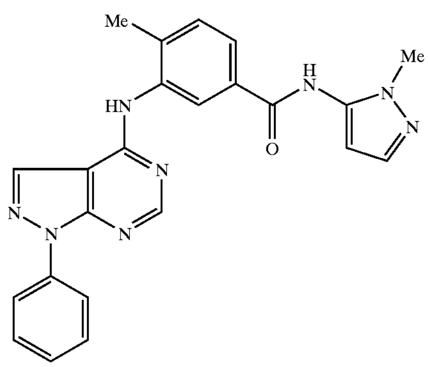 | 425.23 | 1.59[a] |
| 63 | 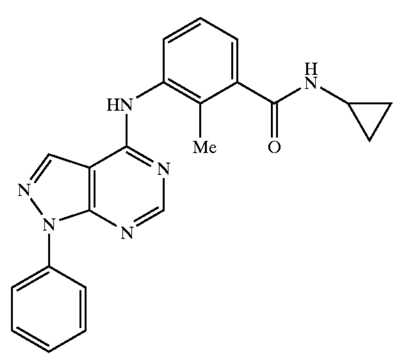 | 385.11 | 1.47[a] |

TABLE 2-continued

| Ex. # | Structure | (M + H)+ | HPLC Retention time (min) |
|---|---|---|---|
| 64 | 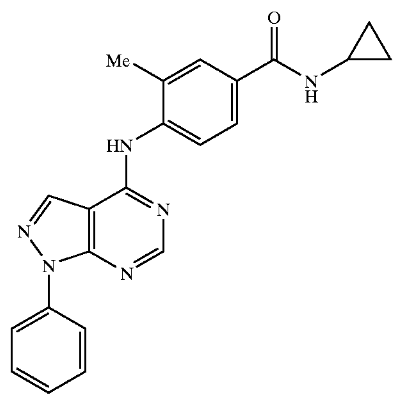 | 385.11 | 1.53[a] |
| 65 | 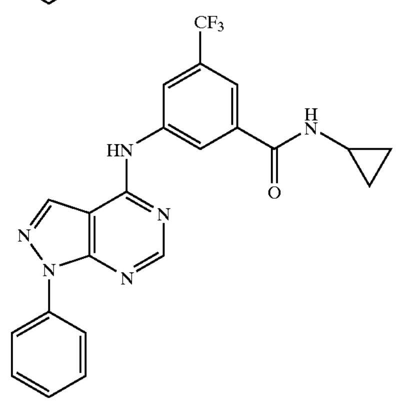 | 439.11 | 2.11[a] |
| 66 | 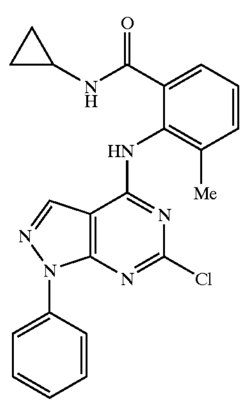 | 419.11 | 1.81[a] |
| 67 | 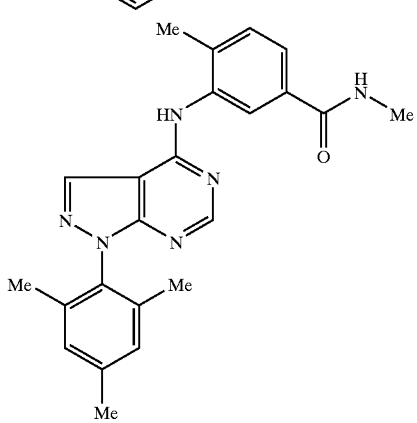 | 401.16 | 2.09[a] |

TABLE 2-continued

| Ex. # | Structure | (M + H)+ | HPLC Retention time (min) |
|---|---|---|---|
| 68 | 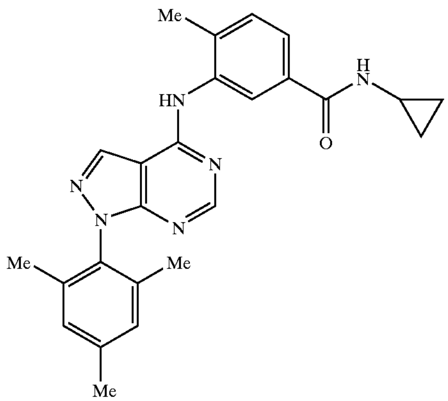 | 427.20 | 2.23[a] |
| 69 | 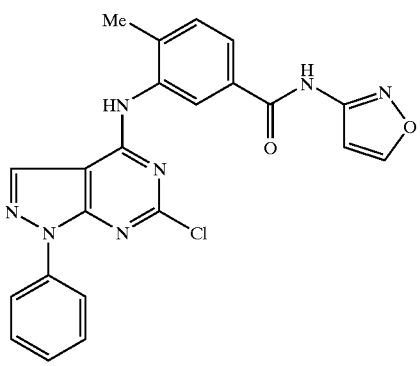 | 446.08 | 1.85[a] |
| 70 | 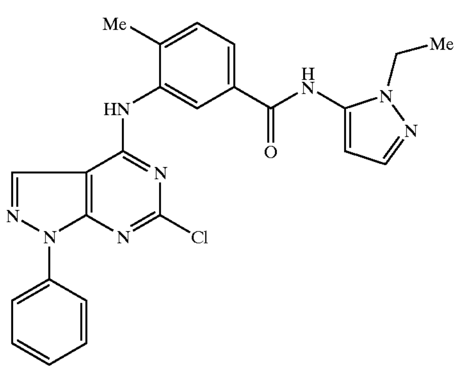 | 473.13 | 1.83[a] |
| 71 | 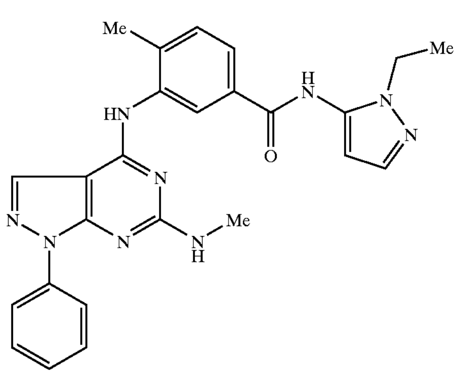 | 468.2 | 1.54[a] |

TABLE 2-continued

| Ex. # | Structure | (M + H)+ | HPLC Retention time (min) |
|---|---|---|---|
| 72 | 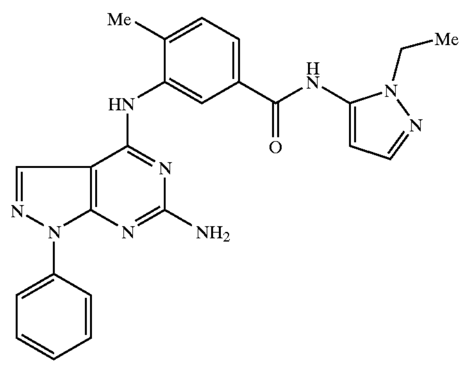 | 454.12 | 1.37[a] |
| 73 | 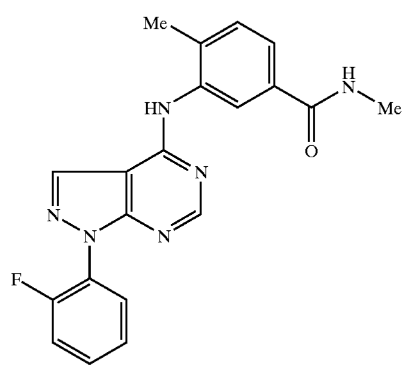 | 377.03 | 1.24[a] |
| 74 | 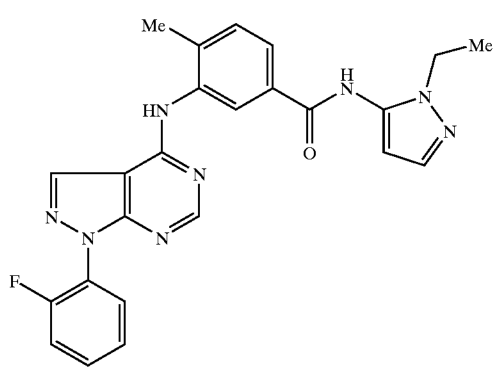 | 457.1 | 1.39[a] |
| 75 | 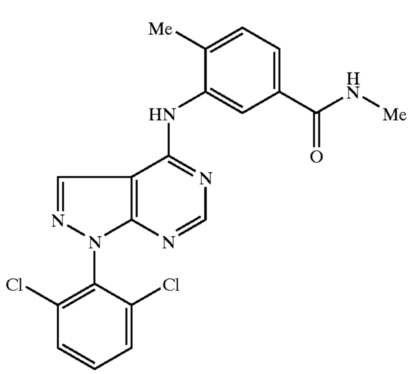 | 426.97 | 1.34[a] |

TABLE 2-continued

| Ex. # | Structure | (M + H)+ | HPLC Retention time (min) |
|---|---|---|---|
| 76 | 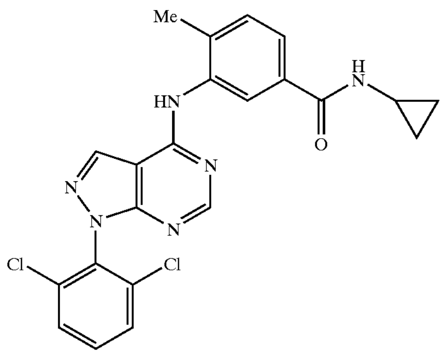 | 453.03 | 1.43[a] |
| 77 | 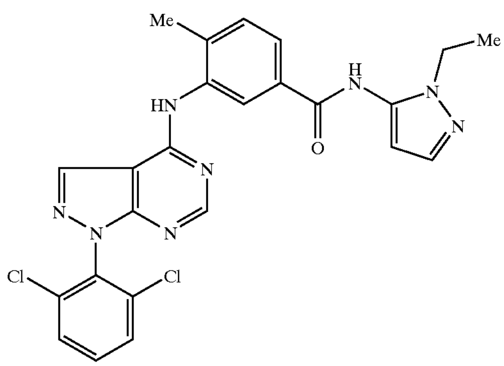 | 507.04 | 1.47[a] |
| 78 | 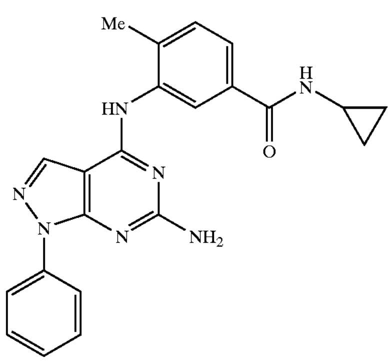 | 400.09 | 1.37[a] |
| 79 | 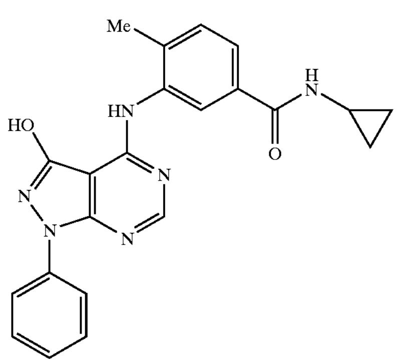 | 401.13 | 1.47[a] |

TABLE 2-continued

| Ex. # | Structure | (M + H)+ | HPLC Retention time (min) |
|---|---|---|---|
| 80 | 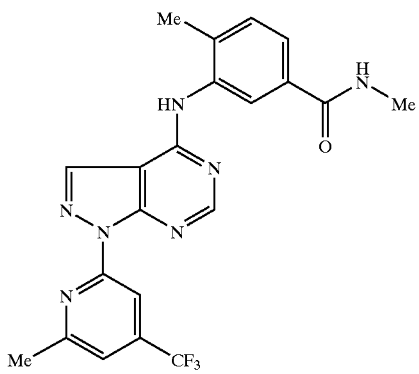 | 442.06 | 1.64[a] |
| 81 | 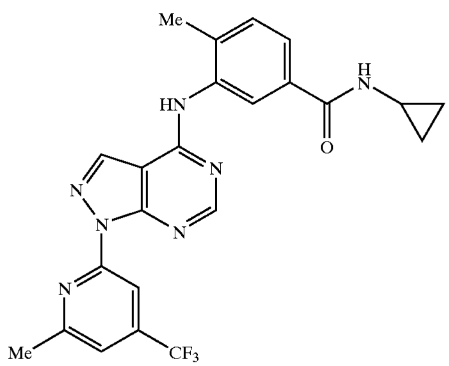 | 468.02 | 1.73[a] |
| 82 | 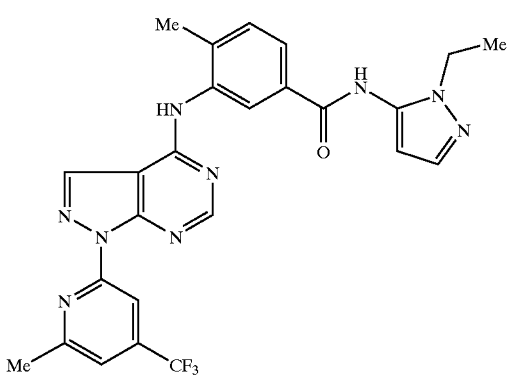 | 522.01 | 1.73[a] |
| 83 | 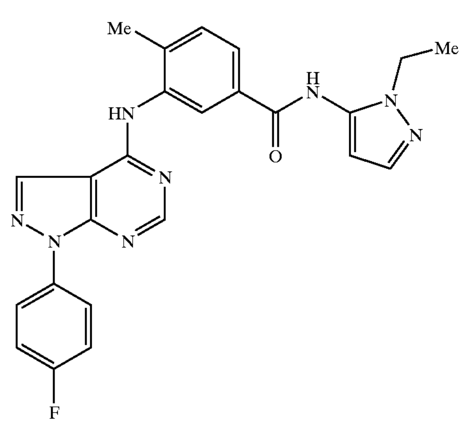 | 457.04 | 1.61[a] |

TABLE 2-continued
| Ex. # | Structure | (M + H)+ | HPLC Retention time (min) |
|---|---|---|---|
| 84 | 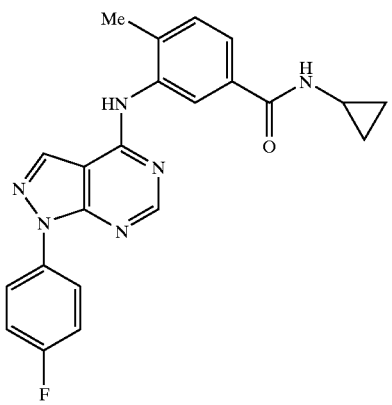 | 403.06 | 1.57[a] |
| 85 | 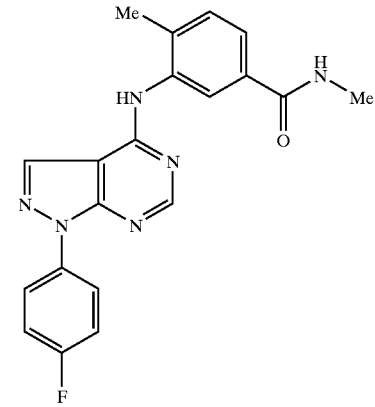 | 377.04 | 1.47[a] |
| 86 | 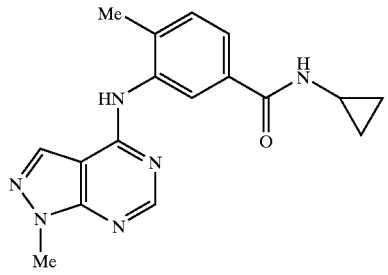 | 337.16 | 0.97[a] |
| 87 | 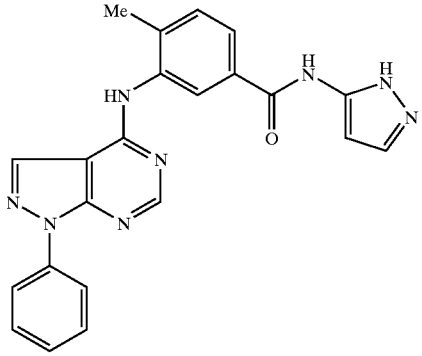 | 413.07 | 1.49[a] |

TABLE 2-continued
| Ex. # | Structure | (M + H)+ | HPLC Retention time (min) |
|---|---|---|---|
| 88 | 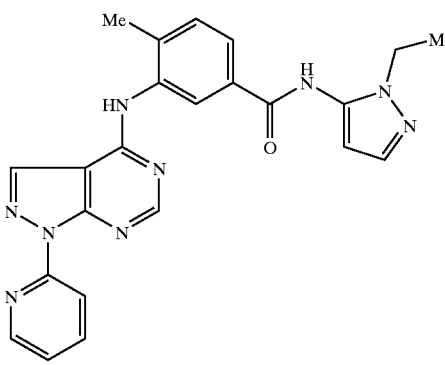 | 440.06 | 1.26[a] |
| 89 | 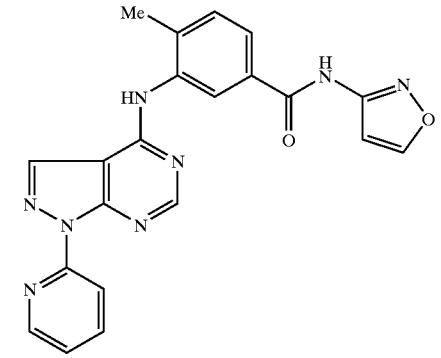 | 413.07 | 1.28[a] |
| 90 | 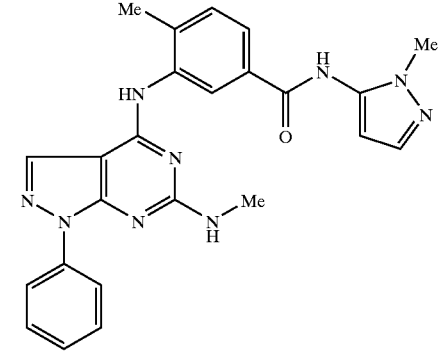 | 454.14 | 1.49[a] |
| 91 | 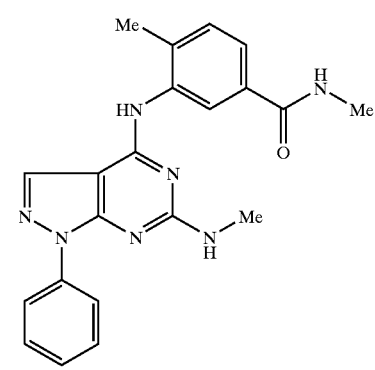 | 388.15 | 1.45[a] |

TABLE 2-continued

| Ex. # | Structure | (M + H)+ | HPLC Retention time (min) |
|---|---|---|---|
| 92 | 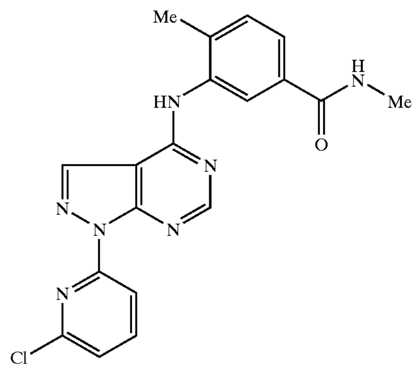 | 394.02 | 1.30[a] |
| 93 | 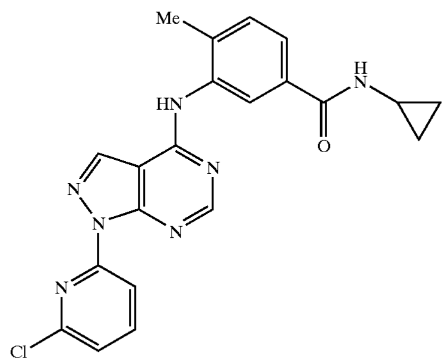 | 420.04 | 1.40[a] |
| 94 | 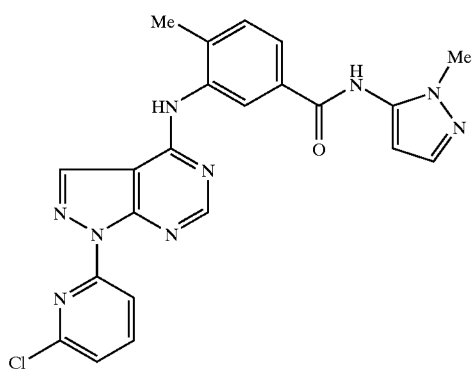 | 460.01 | 1.39[a] |
| 95 | 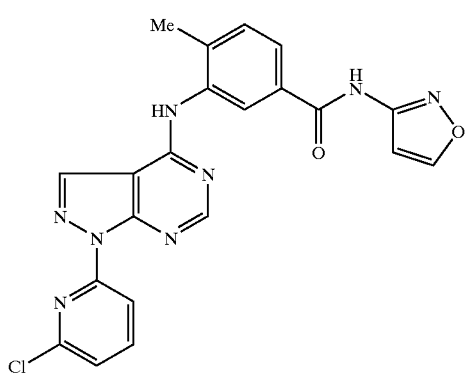 | 446.96 | 1.45[a] |

TABLE 2-continued

| Ex. # | Structure | (M + H)+ | HPLC Retention time (min) |
|---|---|---|---|
| 96 | 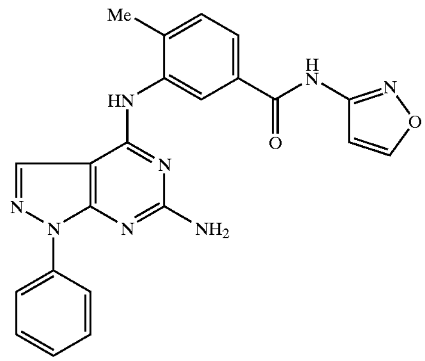 | 427.02 | 1.40[a] |
| 97 | 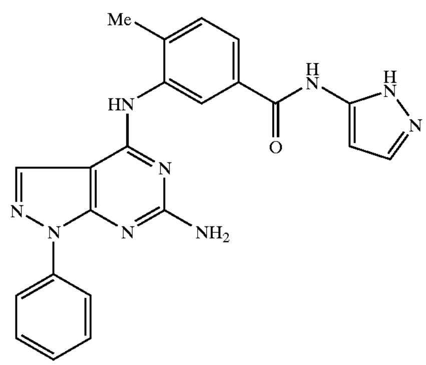 | 426.09 | 1.34[a] |
| 98 | 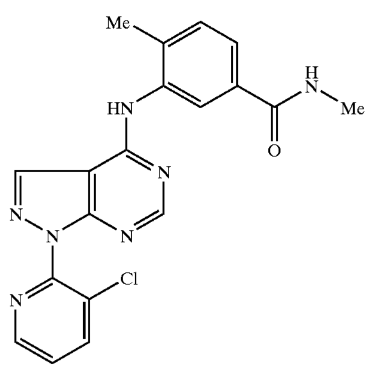 | 393.99 | 1.18[a] |
| 99 | 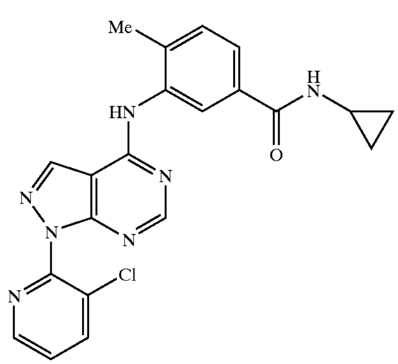 | 420.00 | 1.28[a] |

TABLE 2-continued

| Ex. # | Structure | (M + H)+ | HPLC Retention time (min) |
|---|---|---|---|
| 100 | 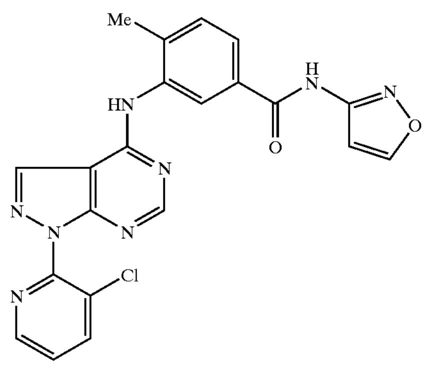 | 446.94 | 1.34[a] |
| 101 | 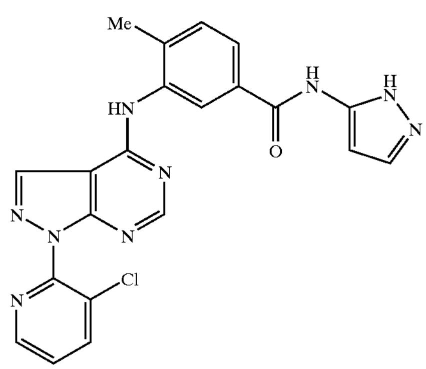 | 459.91 | 1.27[a] |
| 102 | 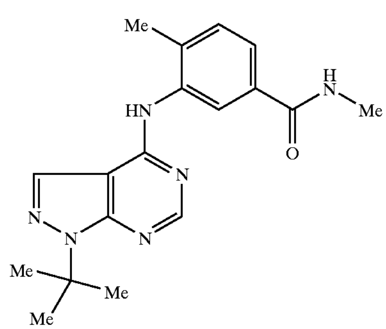 | 339.25 | 1.30[a] |
| 103 | 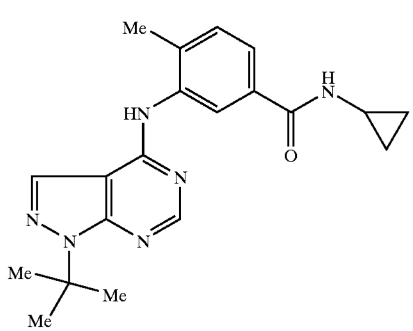 | 365.23 | 1.40[a] |

TABLE 2-continued

| Ex. # | Structure | (M + H)+ | HPLC Retention time (min) |
|---|---|---|---|
| 104 | 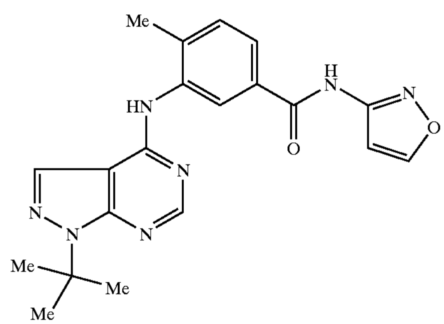 | 392.23 | 1.45[a] |
| 105 | 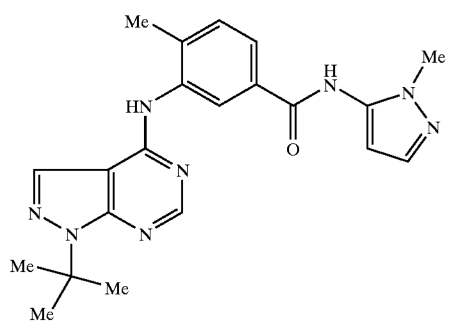 | 405.22 | 1.39[a] |
| 106 | 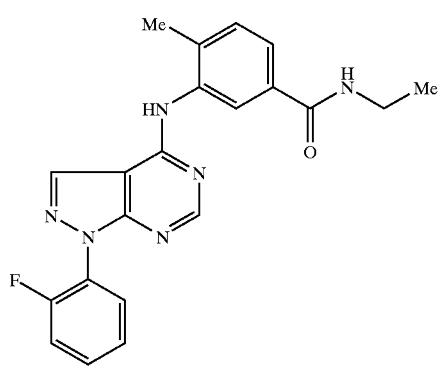 | 391.2 | 1.32[a] |
| 107 | 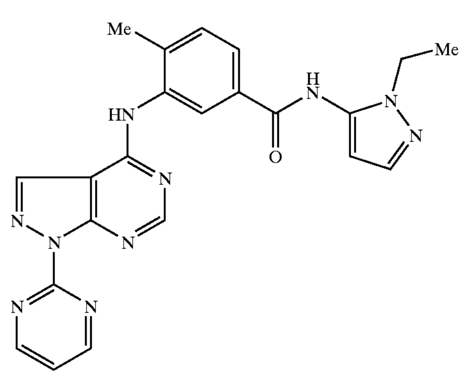 | 441.15 | 1.06[a] |

EXAMPLE 108

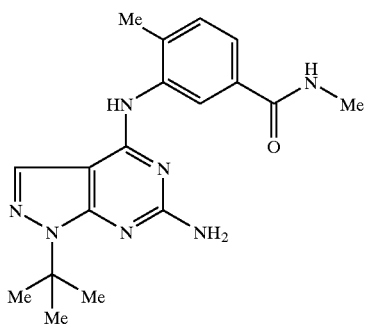

Step A:

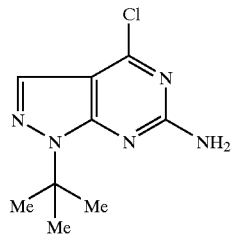
(108A)

A suspension of 2-amino-4,6-dichloro-pyrimidine-5-carboxaldehyde (300 mg, 1.56 mmol) and tert-butylhydrazine hydrochloride (390 mg, 3.13 mmol) in THF (15 mL) and triethyl amine (0.44 mL, 3.13 mmol) was stirred at rt for 5 min and then heated to 64° C. for 40 min. The reaction mixture was concentrated and diluted with water at 0° C. The solid was filtered, washed with water and dried in vacuo over $P_2O_5$ to obtain the title compound 108A (240 mg, 68% yield) as a yellow solid. HPLC retention time: 2.11 min; LC/MS: 226.10 $(M+H)^+$.

Step B:

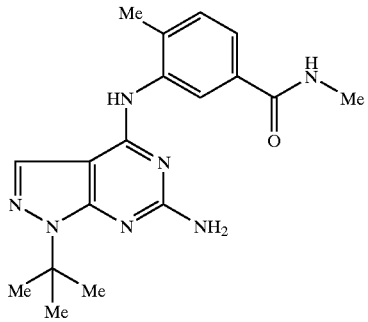
(108)

A solution of compound 108A (40 mg, 0.18 mmol) and compound 2A (37.8 mg, 0.23 mmol) in dimethylformamide (1.7 mL) was heated to 140° C. (oil-bath temp.) for 3.5 h. The solution was cooled to rt and most of the dimethylformamide was removed by distillation in vacuo. The residue was diluted with dimethylsulfoxide/methanol mixture and filtered. The filtrate was purified by reverse phase chromatography on an automated preparative HPLC column: YMC 30×100 mm; Flow rate: 20 mL/min; Gradient time 10 min with 5 min hold; Wave length 220 nm; Starting solvent: 90% solvent A (10% MeOH-90% $H_2O$-0.1% TFA) and 10% solvent B; Final solvent: 90% solvent B (90% MeOH-10% $H_2O$-0.1% TFA) and 10% solvent A. The fraction containing the product was concentrated under Speed Vac™ to obtain the title compound 108 (8.6 mg, 10% yield, orange solid) as a trifluoroacetic acid salt. HPLC retention time: 1.17 min; LC/MS: 354.24 $(M+H)^+$.

EXAMPLES 109–118

Compounds in Examples 109–118 were prepared following the procedure described above for Example 108.

TABLE 3

| Ex. # | Structure | $(M + H)^+$ | HPLC Retention time (min) |
|---|---|---|---|
| 109 | 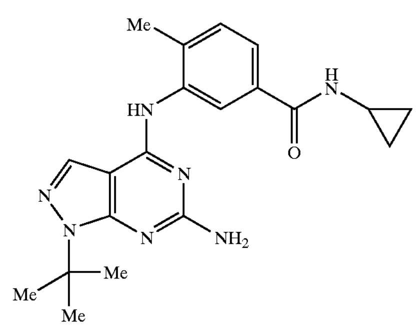 | 380.22 | 1.24[a] |

TABLE 3-continued

| Ex. # | Structure | (M + H)+ | HPLC Retention time (min) |
|---|---|---|---|
| 110 | 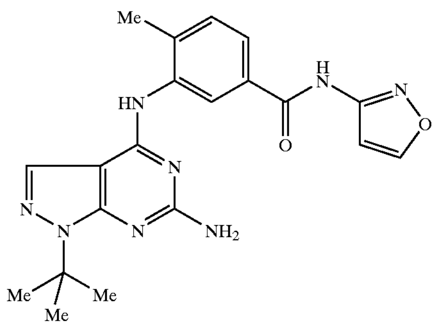 | 407.22 | 1.28[a] |
| 111 | 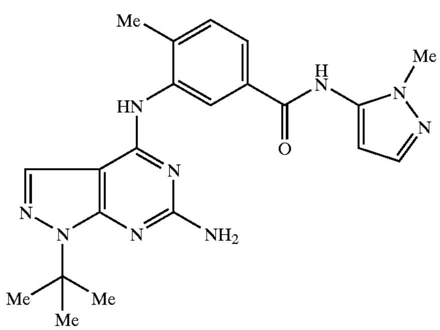 | 420.21 | 1.22[a] |
| 112 | 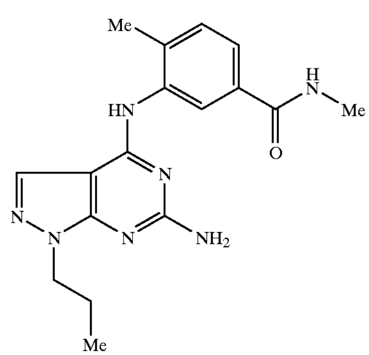 | 340.22 | 1.09[a] |
| 113 | 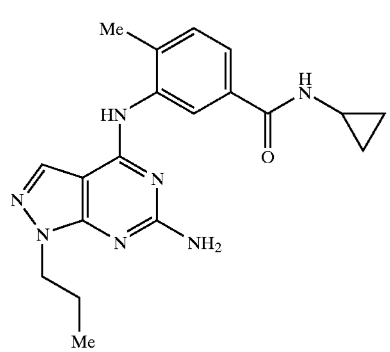 | 366.26 | 1.18[a] |

TABLE 3-continued

| Ex. # | Structure | (M + H)+ | HPLC Retention time (min) |
|---|---|---|---|
| 114 | 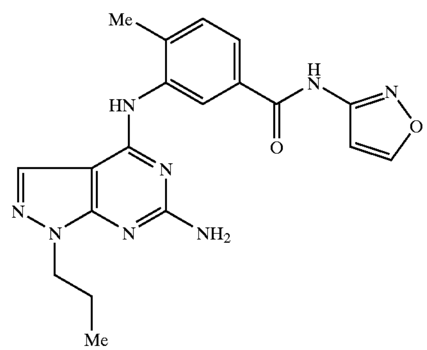 | 393.2 | 1.23[a] |
| 115 | 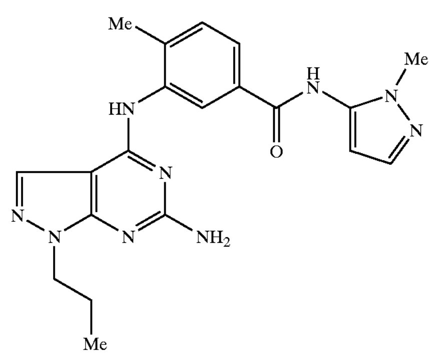 | 406.2 | 1.18[a] |
| 116 | 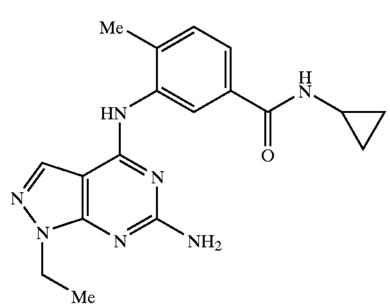 | 352.24 | 1.07[a] |
| 117 | 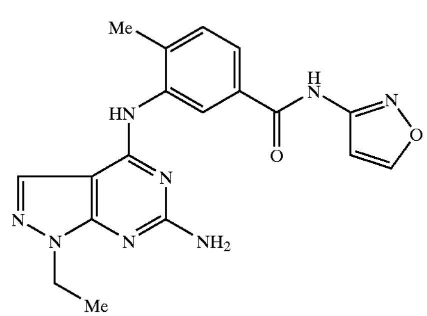 | 379.18 | 1.12[a] |

TABLE 3-continued

| Ex. # | Structure | (M + H)+ | HPLC Retention time (min) |
|---|---|---|---|
| 118 | 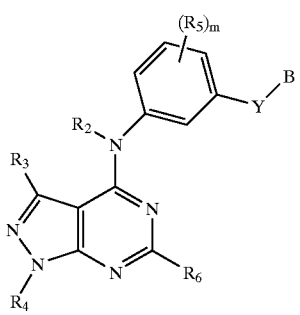 | 392.24 | 1.05[a] |

We claim:

1. A compound having the formula:

$$(I)$$

R3
R2
N
R4
N
N
N
R6
(R5)m
Y
B or a pharmaceutically-acceptable salt or prodrug, thereof, wherein:

Y is —C(=O)NR$_1$—, —NR$_1$C(=O)—, —NR$_1$C(=O)NR$_1$—, —NR$_1$SO$_2$—, —SO$_2$NR$_1$—, —C(=O)—, —OC(=O)—, or —CO$_2$—, provided, however, that when R$_6$ is hydrogen, Y is not —NR$_1$C(=O)—;

B is selected from alkyl, substituted alkyl, alkenyl, substituted alkenyl, hydroxy, alkoxy, aryl, cycloalkyl, heteroaryl, and heterocyclo; or when Y is —C(=O)NR$_1$—, B also may be selected from —C(=O)R$_8$, —C(=O)NR$_8$R$_9$, and —CO$_2$R$_8$, R$_1$ is hydrogen, C$_{1-4}$alkyl, or substituted C$_{1-4}$alkyl;

R$_2$ is hydrogen or C$_{1-4}$alkyl;

R$_3$ is hydrogen, methyl, perfluoromethyl, hydroxy, methoxy, halogen, cyano, NH$_2$, or NH(CH$_3$);

R$_4$ is hydrogen, alkyl, substituted alkyl, alkenyl, substituted alkenyl, aryl, cycloalkyl, heteroaryl, or heterocyclo;

R$_5$ is selected from hydrogen, halogen, cyano, alkyl, substituted alkyl, —C(=O)R$_{11}$, —CO$_2$R$_{11}$, —S(=O)R$_{12}$, —SO$_2$R$_{12}$, —SO$_3$R$_{12}$, —OR$_{11}$, —SR$_{11}$, —NR$_{11}$R$_{12}$, —C(=O)NR$_{11}$R$_{12}$, —NR$_{11}$C(=O)R$_{12}$, NR$_{11}$CO$_2$R$_{12}$, —NR$_{11}$SO$_2$R$_{12}$, —SO$_2$NR$_{11}$R$_{12}$, cycloalkyl, aryl, heterocyclo and heteroaryl;

R$_6$ is selected from halogen, cyano, nitro, A$_1$-R$_{13}$, -A$_1$-O-A$_2$-R$_{13}$, -A$_1$-S-A$_2$-R$_{13}$, -A$_1$-C(=O)-A$_2$-R$_{13}$, -A$_1$-OC(=O)-A$_2$-R$_{13}$, -A$_1$-S(=O)-A$_2$-R$_{13}$, -A$_1$-SO$_2$-A$_2$-R$_{13}$, -A$_1$-CO$_2$-A$_2$-R$_{13}$, -A$_1$-NR$_{13}$-A$_2$-R$_{14}$, -A$_1$-NR$_{15}$C(=O)-A$_2$-R$_{13}$, -A$_1$-NR$_{15}$C(=O)NR$_{16}$-A$_2$-R$_{13}$, -A$_1$-NR$_{15}$CO$_2$-A$_2$-R$_{13}$, -A$_1$-NR$_{15}$SO$_2$-A$_2$-R$_{13}$, -A$_1$-NR$_{15}$SO$_2$NR$_{16}$-A$_2$-R$_{13}$, -A$_1$-SO$_2$NR$_{15}$-A$_2$-R$_{13}$, and -A$_1$-C(=O)NR$_{15}$-A$_2$-R$_{13}$;

A$_1$ is —(CR$_{17}$R$_{18}$)$_r$—;

A$_2$ is —(CR$_{19}$R$_{20}$)$_s$—;

R$_8$ and R$_9$ are selected from hydrogen, alkyl, substituted alkyl, aryl, cycloalkyl, heteroaryl, and heterocyclo, or may form together with the N atom to which these are attached, a heteroaryl or heterocyclo ring;

R$_{11}$, R$_{12}$, R$_{13}$, and R$_{14}$ are selected from hydrogen, alkyl, substituted alkyl, alkenyl, substituted alkenyl, aryl, cycloalkyl, heteroaryl, and heterocyclo, or may form together with the N atom to which these are attached, a heteroaryl or heterocyclo ring, provided that when R$_{12}$ or R$_{13}$ is attached to a sulfonyl group (as in —S(=O)R$_{12}$, —SO$_2$R$_{12}$, —SO$_3$R$_{12}$, -A$_1$-S(=O)R$_{13}$, -A$_1$-SO$_2$R$_{13}$, and -A$_1$-SO$_3$R$_{13}$), R$_{12}$ and R$_{13}$ are not hydrogen;

R$_{15}$ and R$_{16}$ are selected from hydrogen, C$_{1-4}$alkyl, hydroxy, hydroxyC$_{1-4}$alkyl, and aminoC$_{1-4}$alkyl;

R$_{17}$, R$_{18}$, R$_{19}$, and R$_{20}$ are selected from hydrogen, C$_{1-4}$alkyl, halogen, cyano, hydroxy, hydroxyC$_{1-4}$alkyl, haloC$_{1-4}$alkyl, C$_{1-4}$haloalkoxy, amino, C$_{1-4}$alkylamino, and aminoC$_{1-4}$alkyl;

m is 0, 1 or 2; and r and s are selected from 0, 1, 2, 3, and 4.

2. A compound according to claim 1, or a pharmaceutically-acceptable salt, or prodrug thereof, having the formula (Ia),

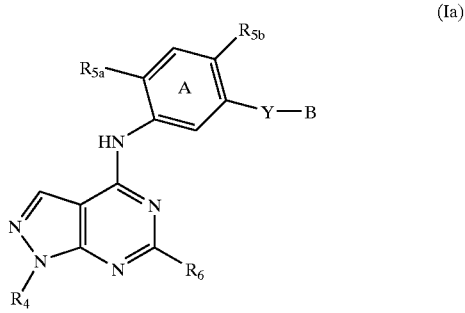

(Ia)

wherein

R$_{5a}$ and R$_{5b}$ are independently selected from hydrogen, C$_{1-4}$alkyl, substituted C$_{1-4}$alkyl, halogen, trifluoromethoxy, trifluoromethyl, hydroxy, C$_{1-4}$alkoxy, cyano, NH$_2$, NH(C$_{1-4}$alkyl), N(C$_{1-4}$alkyl)$_2$, C$_{3-7}$cycloalkyl, five to six membered heteroaryl, four to six membered heterocyclo, phenyl, benzyl, phenyloxy, and benzyloxy.

3. A compound according to claim 2, or a pharmaceutically-acceptable salt or prodrug thereof, in which:

Y is —C(=O)NH—, —NHC(=O)—, —NHC(=O)NH—, —NHSO$_2$—, or —SO$_2$NH—;

B is a hydroxy, alkoxy, cycloalkyl, heteroaryl, heterocyclo, arylalkyl, cycloalkylalkyl, heteroarylalkyl, or heterocycloalkyl;

R$_4$ is alkyl, substituted alkyl, aryl or heteroaryl;

R$_6$ is selected from hydrogen, alkyl, substituted alkyl, halogen, cyano, -A$_1$-O-A$_2$-R$_{13}$, -A$_1$-NR$_{13}$R$_{14}$, —NR$_{13}$-A$_2$R$_{14}$, aryl, cycloalkyl, heteroaryl, and heterocyclo, provided R$_6$ is not hydrogen when B is —NHC(=O)—;

A$_1$ is —(CH$_2$)$_r$—;

A$_2$ is —(CH$_2$)$_s$—; and

R$_{13}$ and R$_{14}$ are selected from hydrogen, alkyl, substituted alkyl, cyano, hydroxy, alkoxy, aryl, cycloalkyl, heteroaryl, and heterocyclo, or may form together with the N atom to which these are attached, a heteroaryl or heterocyclo ring.

4. A compound according to claim 1, or a pharmaceutically acceptable salt or prodrug thereof, in which R$_2$ is hydrogen.

5. A compound according to claim 1, or a pharmaceutically acceptable salt or prodrug thereof, in which R$_3$ is hydrogen.

6. A compound according to claim 1, or a pharmaceutically-acceptable salt or prodrug thereof, wherein R$_4$ is aryl or heteroaryl.

7. A compound according to claim 2, or a pharmaceutically-acceptable salt or prodrug thereof, wherein R$_{5a}$ is halogen or lower alkyl and R$_{5b}$ is hydrogen.

8. A compound according to claim 1, or a pharmaceutically-acceptable salt or prodrug thereof, wherein R$_6$ is selected from —O-A$_2$-R$_{13}$, —NR$_{13}$R$_{14}$, —NR$_{13}$-A$_2$R$_{14}$, aryl, cycloalkyl, heteroaryl, and heterocyclo; and R$_{13}$ and R$_{14}$ are selected from aryl, cycloalkyl, heteroaryl, and heterocyclo, or alternatively, R$_{13}$ and R$_{14}$ taken together form a heterocyclo or heteroaryl ring.

9. A compound according to claim 1, or a pharmaceutically-acceptable salt or prodrug thereof, wherein R$_6$ is alkyl, —O—R$_{13}$, —NR$_{13}$R$_{14}$, morpholinyl, piperidinyl, pyrrolidinyl, piperazinyl, or diazepinyl; and R$_{13}$ and R$_{14}$ are selected from hydrogen, alkyl, hydroxy, hydroxyalkyl, haloalkyl, cyano, cyanoalkyl, morpholinyl, morpholinylalkyl, C$_{3-7}$cycloalkyl, C$_{3-7}$cycloalkylalkyl, pyrrolidinyl, pyrrolidinylalkyl, piperidinyl, piperidinylalkyl, piperazinyl, piperazinylalkyl, wherein each R$_{13}$ and R$_{14}$ group is optionally substituted with one to two groups selected from alkyl, halogen, cyano, hydroxy, C$_{1-4}$alkoxy, amino, lower aminoalkyl, lower alkylamino, and C$_{1-4}$alkyl substituted with one to two hydroxy, halogen, cyano, —O(C$_{1-4}$alkyl), —O(C$_{2-4}$alkenyl), amino, C$_{1-4}$alkylamino, nitro, trifluoromethyl, trifluoromethoxy, —S(C$_{1-4}$alkyl), —SO$_2$C$_{1-4}$alkyl, —CO$_2$H, —CO$_2$(C$_{1-4}$alkyl), —C(=O)H, and/or —C(=O)(C$_{1-4}$alkyl).

10. A compound according to claim 1, or a pharmaceutically-acceptable salt or prodrug, thereof, in which Y is —C(=O)NH—.

11. A compound according to claim 1, or a pharmaceutically-acceptable salt or prodrug thereof, wherein B is selected from —(CH$_2$)$_n$-cycloalkyl, —(CH$_2$)$_n$-(heteroaryl), —(CH$_2$)$_n$-heterocyclo, and —(CH$_2$)$_n$-phenyl, wherein each B is optionally substituted with one to three R$_7$, and in the case of a non-aromatic ring, optionally in addition to one to two R$_7$, B may be substituted with a keto (=O) group;

R$_7$ is selected from C$_{1-6}$alkyl, halogen, trifluoromethoxy, trifluoromethyl, cyano, hydroxy, —OC$_{1-4}$alkyl, —SC$_{1-4}$alkyl, —CO$_2$H, —(CO$_2$)(C$_{1-4}$alkyl), —C(=O)(C$_{1-4}$alkyl), nitro, phenyl, benzyl, phenyloxy, benzyloxy, NH$_2$, NH(C$_{1-4}$alkyl), N(C$_{1-4}$alkyl)$_2$, C$_{3-7}$cycloalkyl, five or six membered heteroaryl or heterocycle, and C$_{1-4}$alkyl substituted with one to two hydroxy, halogen, cyano, —O(C$_{1-4}$alkyl), —O(C$_{2-4}$alkenyl), amino, C$_{1-4}$alkylamino, nitro, trifluoromethyl, trifluoromethoxy, —S(C$_{1-4}$alkyl), —SO$_2$C$_{1-4}$alkyl, —CO$_2$H, —CO$_2$(C$_{1-4}$alkyl), —C(=O)H, and/or —C(=O)(C$_{1-4}$alkyl); and n is 0, 1, 2 or 3.

12. A compound of formula (Ib),

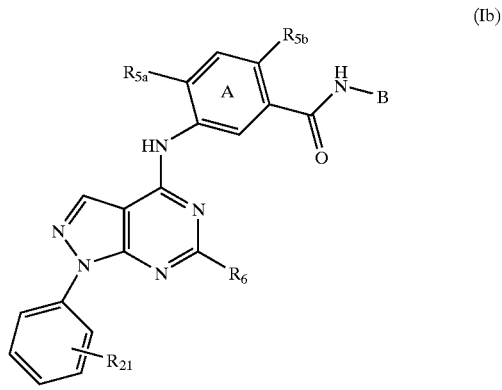

(Ib)

or a pharmaceutically-acceptable salt or prodrug thereof, wherein

B is selected from hydroxy, alkoxy, —C(=O)R$_8$, —C(=O)NR$_8$R$_9$, —CO$_2$R$_8$, —(CH$_2$)$_n$—C$_{3-7}$cycloalkyl, —(CH$_2$)$_n$-heteroaryl, —(CH$_2$)$_n$-heterocyclo, and —(CH$_2$)$_n$-phenyl, wherein each cyclic group B is optionally substituted with one to three R$_7$;

R$_{5a}$ and R$_{5b}$ are independently hydrogen, C$_{1-4}$alkyl, substituted C$_{1-4}$alkyl, halogen, C$_{1-4}$haloalkoxy, C$_{1-4}$haloalkyl, hydroxy, —O(C$_{1-4}$alkyl), or cyano;

R$_6$ is alkyl, —O—(CH$_2$)$_r$—R$_{13}$, —NR$_{13}$R$_{14}$, aryl, cycloalkyl, heterocyclo, or heteroaryl, wherein when R$_6$ is alkyl, aryl, cycloalkyl, heterocyclo, or heteroaryl, R$_6$ is optionally substituted with one to three groups selected from alkyl, substituted alkyl, halogen, cyano, nitro, hydroxy, alkoxy, haloalkoxy, amino, alkylamino, phenyl, benzyl, phenyloxy, and benzyloxy;

R$_7$ and R$_{21}$ are independently selected from C$_{1-6}$alkyl, substituted C$_{1-4}$alkyl, halogen, haloalkyl, haloalkoxy, cyano, nitro, hydroxy, —O(C$_{1-4}$alkyl), phenyl, benzyl, phenyloxy, benzyloxy, NH$_2$, NH(C$_{1-4}$alkyl), N(C$_{1-4}$alkyl)$_2$, C$_{3-7}$cycloalkyl, and five or six membered heteroaryl or heterocycle;

R$_8$ and R$_9$ are selected from hydrogen, alkyl, substituted alkyl, aryl, cycloalkyl, heteroaryl, and heterocyclo, or may form together with the N atom to which these are attached, a heteroaryl or heterocyclo ring;

$R_{13}$ and $R_{14}$ are selected from hydrogen, alkyl, substituted alkyl, cyano, aryl, cycloalkyl, heteroaryl, or heterocyclo, or together form a heterocyclo or heteroaryl ring;

r is 0, 1, 2, 3 or 4; and n is 0, 1, 2, 3, or 4.

13. A compound according to claim 12, or a pharmaceutically acceptable salt or prodrug thereof, in which:

$R_6$ is (i) —$OR_{13}$, or —$NR_{13}R_{14}$; or (ii) alkyl, pyrrolidinyl, morpholinyl, piperidinyl, piperazinyl, or diazepinyl optionally substituted with one to three groups selected from alkyl, hydroxyalkyl, cyanoalkyl, haloalkyl, haloalkoxy, halogen, cyano, hydroxy, alkoxy, amino, aminoalkyl, and alkylamino; and $R_{13}$ and $R_{14}$ are selected from hydrogen, alkyl, hydroxyalkyl, cyano, cyanoalkyl, morpholinylalkyl, $C_{3-7}$cycloalkyl, $C_{3-7}$cycloalkylalkyl, pyrrolidinyl, pyrrolidinylalkyl, piperidinyl, piperidinylalkyl, wherein each $R_{13}$ and $R_{14}$ group in turn is optionally substituted with one to two groups selected from $C_{1-6}$alkyl, substituted $C_{1-6}$alkyl, halogen, cyano, hydroxy, —O($C_{1-4}$alkyl), amino, and $C_{1-6}$alkylamino.

14. A compound according to claim 12, or a pharmaceutically acceptable salt or prodrug thereof, in which B is phenyl optionally substituted with one to two $R_7$; cycloalkyl optionally substituted with keto and/or one to two $R_7$; or B is selected from one of:

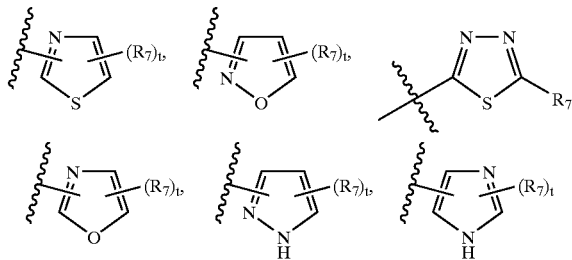

-continued

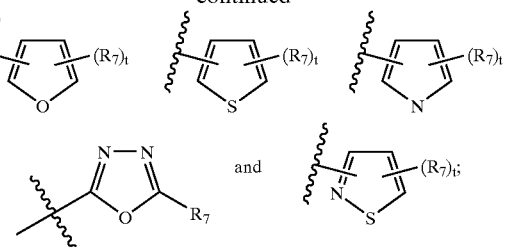

and $R_7$ is hydrogen, $C_{1-4}$alkyl, trifluoromethyl, trifluoromethoxy, halogen, cyano, amino, —($C_{1-4}$alkyl)amino, hydroxy, —O($C_{1-4}$alkyl), phenyl, benzyl, phenyloxy, or benzyloxy, or two $R_7$ groups attached to adjacent carbon atoms or an adjacent carbon and nitrogen atom may join to form a fused heterocyclo or carbocyclic ring, said fused ring in turn being optionally substituted with one to two of $C_{1-4}$alkyl, trifluoromethyl, trifluoromethoxy, halogen, cyano, amino, —($C_{1-4}$alkyl)amino, hydroxy, —O($C_{1-4}$alkyl), phenyl, benzyl, phenyloxy, and benzyloxy; and t is 2 or 3.

15. A pharmaceutical composition comprising at least one compound according to claim 1 and a pharmaceutically-acceptable carrier or diluent.

16. A pharmaceutical composition comprising at least one compound according to claim 12 and a pharmaceutically-acceptable carrier or diluent.

17. A method of treating from rheumatoid arthritis, psoriatic arthritis, traumatic arthritis, rubella arthritis, gouty arthritis and/or osteoarthritis in a patient comprising administering to the patient a pharmaceutical composition according to claim 15.

* * * * *